(12) United States Patent
Eros et al.

(10) Patent No.: US 7,728,042 B2
(45) Date of Patent: Jun. 1, 2010

(54) TRANSDERMAL PHARMACEUTICAL COMPOSITION

(75) Inventors: Istvan Eros, Szeged (HU); Ildiko Pannonhalmine Csoka, Deszk (HU); Erzsebet Soosne Csanyi, Szeged (HU); Attila Bodis, Budapest (HU); Erzsebet Lapis, Budapest (HU); Erzsebet Francsicsne Czinege, Budapest (HU); Emoke Kissne Csikos, Budapest (HU); Janos Illes, Budapest (HU)

(73) Assignee: Richter Gedeon Vegyeszeti Gyar RT, Budapest (HU)

( * ) Notice: Subject to any disclaimer, the term of this patent is extended or adjusted under 35 U.S.C. 154(b) by 158 days.

(21) Appl. No.: 10/575,145

(22) PCT Filed: Oct. 6, 2004

(86) PCT No.: PCT/HU2004/000092
§ 371 (c)(1),
(2), (4) Date: Mar. 23, 2007

(87) PCT Pub. No.: WO2005/032514
PCT Pub. Date: Apr. 14, 2005

(65) Prior Publication Data
US 2007/0264345 A1 Nov. 15, 2007

(30) Foreign Application Priority Data
Oct. 9, 2003 (HU) .................. 0303313

(51) Int. Cl.
*A61K 31/12* (2006.01)
(52) U.S. Cl. .................. 514/675; 424/400
(58) Field of Classification Search .............. None
See application file for complete search history.

(56) References Cited

U.S. PATENT DOCUMENTS

| 5,326,566 A | * | 7/1994 | Parab ............... 424/401 |
| 5,523,093 A | | 6/1996 | Della Valle et al. |
| 5,616,568 A | * | 4/1997 | Pouyani et al. ........ 514/54 |
| 5,985,850 A | | 11/1999 | Falk et al. |
| 6,069,135 A | | 5/2000 | Falk et al. |
| 2004/0192620 A1 | * | 9/2004 | Bunschoten et al. ...... 514/26 |

OTHER PUBLICATIONS

Brynhildsen et al. Low dose transdermal estradiol/nonethisterone acetate treatment over 2 years does not cause endometrial proliferation in postmenopausal women. Menopause.9(2):137-144, Mar. 2002.*
Liquid Crystals and Their Applications in Drug Delivery (American Cyanamid Corporation), 1989.

* cited by examiner

*Primary Examiner*—Ardin Marschel
*Assistant Examiner*—Amy A Lewis
(74) *Attorney, Agent, or Firm*—Jonathan Myers; Andrew Wilford

(57) ABSTRACT

The invention relates to a liquid crystal gel containing polyoxyethylene-glyceryl-trioleate, propylene-glycol, isopropyl myristate and a hyaluronic acid salt or complex for use in the manufacture of transdermal pharmaceutical compositions and healing cosmetics. The invention also relates to transdermal pharmaceutical composition consists of an estrogen and a progestin component as well as a liquid crystal gel containing polyoxyethylene-glyceryl-trioleate, propylene-glycol, isopropyl myristate and a hyaluronic acid salt or complex. The invention can be applied for transdermal hormone replacement therapy and for other transdermal depending on the active principles included.

30 Claims, 9 Drawing Sheets

TRANSDERMAL PHARMACEUTICAL COMPOSITION

CROSS REFERENCE TO RELATED APPLICATIONS

Figure 1:
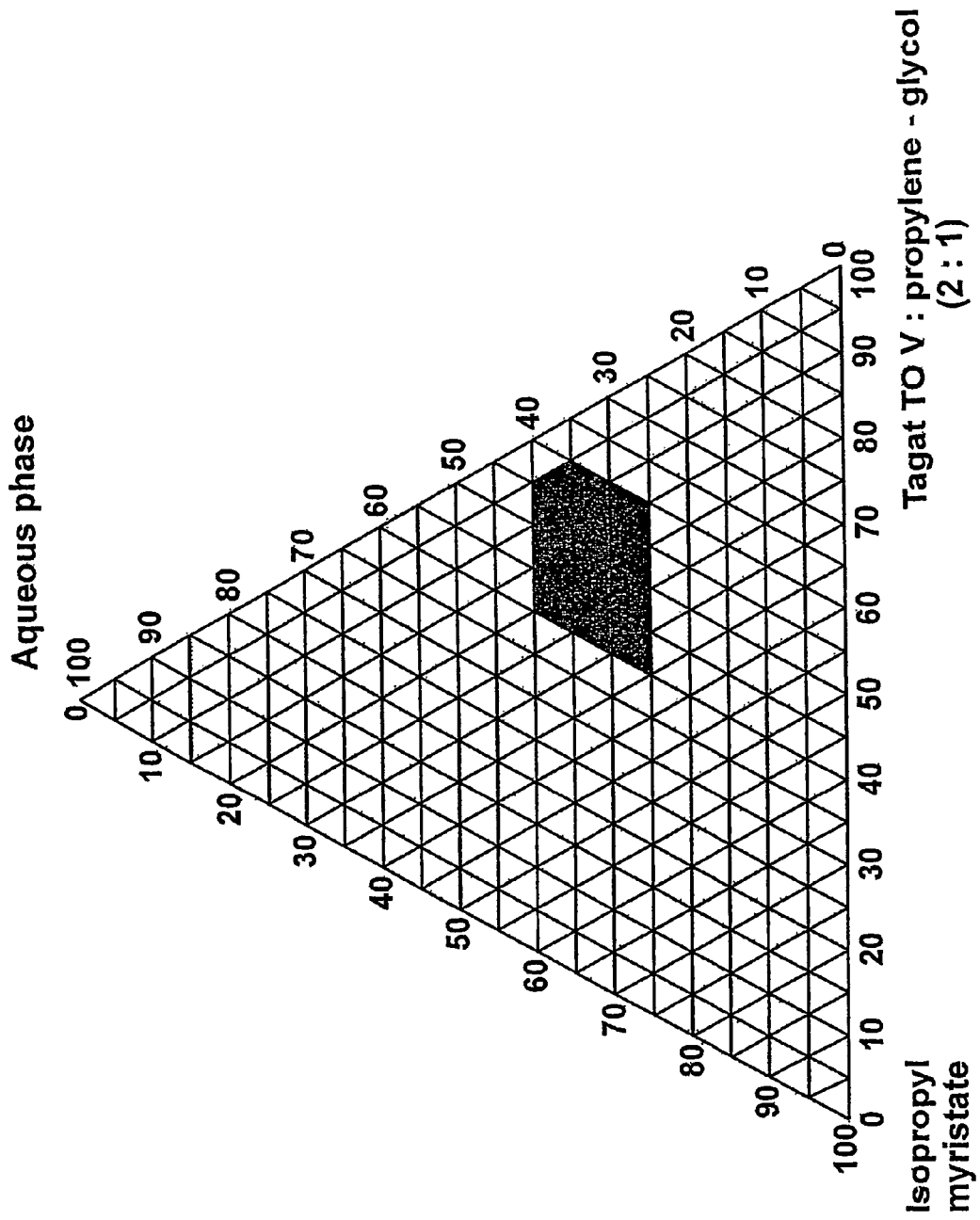

This application is the US national phase of PCT application PCT/HU2004/000092, filed 6 Oct. 2004, published 14 Apr. 2005 as WO 2005/032514, and claiming the priority of Hungarian patent application P0303313 itself filed 9 Oct. 2003.

The invention relates to a liquid crystal gel containing polyoxyethylene-glyceryl-trioleate, propylene-glycol, isopropyl myristate and a hyaluronic acid salt or complex for use in the manufacture of transdermal pharmaceutical compositions and healing cosmetics.

The invention also relates to transdermal pharmaceutical composition consists of an estrogen and a progestin component as well as a liquid crystal gel containing polyoxyethylene-glyceryl-trioleate, propylene-glycol, isopropyl myristate and a hyaluronic acid salt or complex.

The invention also relates to method of treatment for transdermal hormone replacement therapy, where a pharmaceutical composition consists of an estrogen and a progestin component as well as a liquid crystal gel containing polyoxyethylene-glyceryl-trioleate, propylene-glycol, isopropyl myristate and a hyaluronic acid salt or complex is applied onto the surface to be treated.

The invention also relates to transdermal pharmaceutical composition consists of one or more active agent components (among others, ondansetron, terbinafine, fluconazole, metronidazole, fentanyl, nandrolone decanoate, nestorone, norethisterone, eperisone, tolperisone, vinpocetine, ketamine, vincristine, vinblastine) as well as a liquid crystal gel containing polyoxyethylene-glyceryl-trioleate, propylene-glycol, isopropyl myristate and a hyaluronic acid salt or complex.

The invention also relates to method of treatment for transdermal therapies, where a pharmaceutical composition consists of one or more active agent components (among others, ondansetron, terbinafine, fluconazole, metronidazole, fentanyl, nandrolone decanoate, nestorone, norethisterone, eperisone, tolperisone, vinpocetine, ketamine, vincristine, vinblastine) as well as a liquid crystal gel containing polyoxyethylene-glyceryl-trioleate, propylene-glycol, isopropyl myristate and a hyaluronic acid salt or complex is applied onto the surface to be treated.

Dermatological application of liquid crystal systems as valuable and potential base of ointment was first proposed by Wahlgreen, S. et al. in 1984 (J. Pharm. Sci., Vol. 73. 1984. p. 1484).

The application of liquid crystal and microemulsion systems in drug formulation was described in several publications. The concept of microemulsion and microemulsion gel was clarified by Nürnberg, E. and co-workers (Dtsch. Apoth. Ztg., Vol. 123. 1983. p. 1933; Pharm. Ind., Vol. 48. 1986. p. 1191; Pharm. Acta. Helv., Vol. 65. 1990. p. 105), and the applicability of these systems in drug formulation was also emphasized.

The characterization of microemulsions and microemulsion gels by rheological investigations and the physicochemical background of their formation was elaborated by Stupar, M. and co-workers (Pharmazie, Vol. 41. 1986. p. 516).

The techniques of controlled drug delivery were collected, systemized and published in a monograph in 1989 by Tyle, P. and co-workers (Ed.: Roshoff, M.; Controlled Release of Drugs: Polymers and Aggregate Systems, VCH Publishers Inc., 1989. pp. 125-162; Liquid Crystals and Their Application in Drug Delivery). The monograph deals with liquid crystal systems (when surface-active agents form specific aggregates), their classification, possibilities as well as with their stability and applications.

Surfactants are surface-active or capillary active agents, consisting of a polar and a nonpolar portion within the same organic compound. It is important, that these two parts are asymmetrically positioned. Usually surfactants significantly lower the surface tension of water, and used as emulsifiers, moisturizing agents and solubilizing additives in drug formulation.

Cosurfactants are organic molecules that have no or much lower surface-activity than surfactants, but help their function and thus the quantity of surfactants can be reduced. Surfactants are physiologically not indifferent and can harm skin as well as mucosa in higher concentration.

Systems produced from surface-active agents are usually classified as two- or multicomponent systems.

Two-component systems consist of one or two surfactants and a solvent (usually water) and can be classified as systems with low or high degree of association. Liquid crystals fall between them, in terms of association.

Micelles, inverse micelles and polymer micelles are systems with low degree of association. Biological membranes and lipoproteins are systems with high degree of association. Liquid crystal systems have medium degree of association (Vyas, S. P. et al, Pharmazie, Vol. 52. 1997. p. 259). Their arrangement is identical with that of crystalline solids.

Diverse systems are formed depending on the concentration of the solvent. These systems were classified by Brown, G. H. and Wolken, J. J., (Liquid Crystals and Biological Structures, Academic Press, New York, 1979) as follows:

| | | |
|---|---|---|
| 0% | water | crystalline state, compact solid substance |
| 5-22% | water | lamellar liquid crystal state |
| 23-40% | water | liquid crystal state, arrayed in cubic lattices |
| 34-80% | water | liquid crystal state, hexagonal phase |
| 30-99.9% | water | micellar solution |

Microemulsions and microemulsion gels are multicomponent systems (at least 3, usually 4 components). There is a high similarity between microemulsions and liquid crystals, but their compositions differ from each other. Microemulsions consist of at least three components: a surfactant (occasionally combined with cosurfactant), oil and water. Microemulsions are fluid, clear, transparent, isotropic, thermodynamically stable systems, according to the definition of Nürnberg, E. (Pharm. Acta. Helv., Vol. 65. 1990. p. 105). They contain at least one surfactant, more frequently the mixture of two surfactants and consist of two immiscible or partially miscible liquids. Their existence requires a critical ratio of the three components.

Microemulsion gels retain their shape at room temperature, but they are spreadable and usually viscoelastic systems with high viscosity. They consist of a surfactant, a cosurfactant, oil as lipophilic component and water. Macroscopically they display transparency or slight opalescence. Microemulsion gels are optically isotropic and thermodynamically stable systems.

Microemulsions and microemulsion gels are spontaneously formed at a certain relative amount of the surfactant (occasionally combined with cosurfactant), the oil and the water.

The relative amounts required for the formation of microemulsions and microemulsion gels can be determined by phase diagrams. The regions of these ternary phase diagrams show the system and the structure that correspond to a certain relative amounts of the three components. The three sides of the triangle indicate the concentration of the surfactant and the cosurfactant together, the concentration of the oil phase, and that of the water phase, respectively. The concentration range of the components resulting in the formation of microemulsion or microemulsion gel can be determined experimentally on the basis of the diagram.

The characteristics of microemulsion systems (optical isotropy or anisotropy, structure, viscosity as well as stability) can be studied by optical, rheological and thermoanalytic techniques.

The molecular arrangement (crystal-like property) can be proven by the application of polarization microscope. As proof of the liquid crystal state, a typical interference pattern ('Maltese cross') is displayed by a high magnification imaging microscope with computer connection.

The coherent structure can be proven by rheological technique, and the presence of liquid crystals can be quantitatively described by a relatively simple method (Schambil, F. and co-workers: Fette und Öle, Vol. 144. 1988. p. 295). Namely, by increasing the surfactant concentration in solution, a dramatic increase in viscosity occurs at a given concentration.

Hormone replacement therapy (HRT) involves the administration of estrogen as well as that of the combination of estrogen and progestin for the treatment of menopausal syndrome and for the prevention of cardiovascular diseases and osteoporosis. The hormones given as medication in HRT are similar to the female sex hormones produced prior to menopause. The HRT applied during or at the onset of menopause restores the physiological equilibrium of female sex hormones, i.e. estrogens and progestins. Consequently plasma concentrations of sex hormones are normalized and increased to the level of reproductive years by medication and hereby somatic and emotional complaints are relieved. HRT has been applied since the nighteen-fifties as effective treatment of menopausal syndrome.

The advantages of the application of HRT in menopause were summarized by Christiansen, C. (Maturitas, Vol. 38. Suppl. 1. 2001). Early symptoms of menopausal syndrome, vasomotor complaints, hot flashes and psychical disorders as well as the symptoms that are due to estrogen deficiency, i.e. vaginal dryness, painful intercourse, frequent and urgent need to pass urine in consequence of mucosal change at the lower urinary tract as well as different urinary complaints are abolished by HRT within a short period of time. In addition, urinary incontinence after menopause is also relieved by HRT.

Beside symptomatic improvement, HRT has additional advantages, in the case of long-term application: prevention of the development of osteoporosis, cardiovascular diseases, Alzheimer-disease and colon cancer as well as the improvement of post-menopausal women's quality of life.

The application of progestins in HRT has primarily a protective role. Besides contributing to the abatement of some symptoms as well as their occasional administration alone, the application of progestins is primarily justified by their protection against the side-effects of estrogens. Their administration is compulsory in order to protect against the endometrial proliferating effect as well as the risk of secondary endometrial carcinoma increasing potency of estrogens.

In HRT, progestins are employed in a sequential or continuous manner. Both forms of therapy are effective for the protection of endometrium. Sequential therapy involves withdrawal bleeding which resembles a menstrual period, since the administration duplicates the pattern of plasma levels of hormones in women of fertile age. The progestin is given for a definite number of days of the menstrual cycle in higher dose compared to the continuous combined administration. In this case, the undesirable effects of progestins (nausea, breast tenderness, breast tension, headache, withdrawal bleeding) arise more frequently. Menstrual bleeding can be eliminated by HRT performed by means of continuous combined administration of small doses of progestins and therefore adverse effects caused by progestins can be relieved.

For HRT, natural estrogens (estradiol, estrone, estrone sulphate, estriol) as well as conjugated and equino-estrogens are used; most of the latter ones are produced by chemical synthesis.

Estradiol is the most effective estrogen. The efficacy of estrone is lower by 50-70%; estriol is the least effective among the three classical estrogens, its activity is 10% as compared to that of estradiol.

The effects of estrogens were described by Ruggiero, R. J. and Likis, E. (J. Midwifery Womens Health, Vol. 47. 2002. p. 130). Estrogens performs both short-acting effects by means of non-genomic mechanisms and late effects taking place by the mediation of genomic mechanisms. It is supposed, that estrogens act by the regulation of gene expression. Estrogens entering the cells of estrogen-responsive tissues (breast, hypothalamus, pituitary) are bound to intracellular receptors. Estrogen receptors fall within the superfamily of nuclear hormone receptors and interact with specific nucleotide sequences of the influenced genes. The latter increase the transcription of the regulated gene. Estrogen action in certain tissues is manifested mainly in direct activation of one or several genes (e.g. in the sharp increase in the synthesis and/or secretion of proteins). In the case of more complex reactions (endometrial proliferation, increase of bone substance) the estrogen receptor starts the transcription of a finite number of complicated 'quick-reacting' genes and the products formed initiate a series of secondary events resulting in tissue response. The acute, non-genomic effect of estradiol is mediated by the estrogen receptors of the plasma membrane.

In the course of HRT the estradiol administered is able to replace all physiological effects of endogenous estradiol. Estradiol applied in HRT increases the cervical secretion, the endometrial proliferation as well as the tone of myometrium. Early symptoms of estrogen deficiency, vasomotory symptoms, hot flushes, night sweating as well as racing heart (palpitation) are abolished. Estradiol applied in HRT performs its favourable effect on psychic disorders by increasing the endogenous opioid production, the displacement of triptophane bound to plasma proteins as well as by reducing the increased monoaminooxidase activity in the CNS. Estradiol therapy applied in HRT acts on the estrogen receptors of the urogenital tract and therefore significantly decrease the vaginitis of old age, urethral insufficiency, the incidence of painful intercourse as well as that of urinary incontinence after menopause, namely the atrophy of the mucosa of the urogenital tract.

An important physiological effect of estrogens is the inhibition of activation of the metabolic unit of bone-tissue. Estrogen inhibits the synthesis of interleukins (IL), which are formed in bone-forming osteoblasts and efficiently stimulate the resorption of bone. In addition, estrogen inhibits the activity of IL-6 and retards the bone resorption-stimulating effect of parathyroid hormone at receptor level the latter is presumably connected to its effect on interleukins. The metabolism of minerals is also influenced by the systemic effects of estrogens and hereby the maintenance of calcium homeostasis is assisted. Among others, they intensify the activity of the hydroxylating enzyme activating vitamin D to 1,25-dihydroxy-cholecalciferol in the kidney.

The adverse consequences of menopause are abolished by estradiol applied in HRT by a complex mechanism. Hormone-mediated vasodilatation is induced within a few minutes after the administration of estradiol. The expression of genes coding for various vasodilatating substances might be increased, the lipid composition of plasma might favourably be modified and hereby the progression of arteriosclerosis may also be moderated by the estradiol effects of longer latency. The total cholesterol and LDL (low-density lipoproteins) plasma levels are lowered, the HDL-cholesterol (high-density lipoproteins) levels, especially that of the $HDL_2$-fraction are raised by estradiol. The increase of HDL-cholesterol level is attributed to the inhibition of hepatic lipase activity. The decrease of LDL-cholesterol level is due to the increase of cholesterol uptake from the plasma in consequence of the increase of LDL receptor expression both in liver and peripheral tissues.

The plasmatic triglyceride level might be increased by orally administered estrogens due to the increase of hepatic production of VLDL (very-low-density lipoproteins). In addition, the formation of triglycerides from carbohydrates and free fatty acids is also promoted by the increase of sensitivity of peripheral tissues to insulin.

In consequence of estrogen replacement, the blood lipid profile is favourably altered, namely its artherosclerosis-inducing effect is decreased. Estrogens have further, essentially cardioprotective effects, too, on blood clotting (antithrombin activity and/or platelet aggregation is decreased), on carbohydrate metabolism (fasting blood sugar is raised), on blood pressure (renin substrate supply is increased) or on vascular tone (presumably by the increase of local prostacycline production).

The fasting glucose and insulin levels of non-diabetic women are lowered by HRT. After menopause, HRT improves the sensitivity of tissues to insulin in women suffering from type 2 diabetes.

The cutaneous atrophy of women after menopause is the result of the decrease of collagen and hyaluronic acid in the skin. Estrogen functions as the inductor of hyaluronic acid synthase, therefore the synthesis of the high molecular mass hyaluronic acid is increased in HRT, and the water content of the connective tissue of the skin is increased.

The effects of progestins applied in HRT were summarized by Sitruk-Ware, R. (J. Steroid Biochem. Molec. Biol., Vol. 69. 1999. p. 185). The progestins applied in HRT take their effects by binding to specific receptors. They influence reproductive functions of the female organism and the endometrial transformations. They have effect on metabolism of bone and increase the bone tissue preserving potency of estrogens. Through their metabolic effects, progestins stimulate the activity of lipoprotein lipase which leads to lipid deposition, increases the LDL-C level and decreases the HDL-C level resulting in increased risk of cardiovascular diseases. Since estrogens have opposite actions, the cardiovascular disease decreasing effect of estrogens is diminished by progestins. There are no adequate data that would indicate if the risk of breast cancer is increased by progestins or not. Some data indicate that the administration of progestins in a cyclic manner increases the risk.

From among progestins, pregnane derivatives (medroxyprogesterone acetate) and 19-nortestosterone derivatives (norethindrone) are widely used in HRT. It is known, that the risk of cardiovascular diseases are decreased by high HDL-cholesterol level and increased by high LDL-cholesterol level. Although the estrogen component of HRT preparations increases the HDL-cholesterol level and the HDL/LDL ratio, these favourable effects are weakened by progestins in consequence of their androgenic action, or even the processes are shifted to the adverse direction. These unfavourable effects are eliminated by the application of new, selective, second and third generation progestin components, which are free from androgenic actions (gestodene, etonogestrel, levonorgestrel).

In HRT, the application of new and selective progestins being free from androgenic actions ensures that there is no unfavourable change in the proportion of plasma lipids i.e. the favourable HDL/LDL ratio induced by the estrogen component is maintained (Sobel, N. B.: Obstet. Gynecol. Clin. North Am., Vol. 21. 1994. p. 299). Within HDL, the levels of the $HDL_2$-subfraction are not decreased either, which is of outstanding importance from the point of view of cardiovascular diseases and has a favourable effect on the symptoms of hyperandrogenaemia (androgenic type alopecia, hirsutism).

Compared to that of the oral administration, the pharmacokinetic profile of tansdermal administration (transdermal gels, patches) is more advantageous (Stevenson, J. C.: Maturitas, Vol. 33. 1999. S31). In the case of oral ingestion, a higher dose of hormone is required since the 90% of hormones are transformed into less active estrone and conjugated metabolites in the gastrointestinal tract and the liver, therefore the plasma level of estrone becomes higher than that of estradiol. In the case of transdermal administration, the biotransformation in the skin is much less extensive, therefore the hormone can be applied in lower doses and the plasmatic estradiol/estrone ratio yields the physiological state prior to menopause. When HRT preparations are orally administered, in consequence of periodically and abruptly high plasmatic hormone levels, the synthesis of various proteins (renin substrate, blood clotting factors) are induced in portal circulation, which is responsible for the side-effects observed. In the case of transdermal application of HRT, it should be emphasized that there is no increase in renin substrate synthesis, or any change in the function of blood clotting system, insulin metabolism and the triglyceride levels do not increase. These differences decrease the risk of cardiovascular diseases in the case of transdermal application, therefore transdermal administration is favourable for some patients such as women suffering from unstable hypertension or hypertriglyceridaemia as well as women with a history of thromboembolism.

Concerning breast cancer, the low-dose transdermal estrogen treatment provides the highest safety since the stimulating effect on formation of metabolites (which can be potentially oncogenic) is minimal.

HRT is applied by means of patches and gels. Applying patches, skin reactions manifested by irritation, erythema, allergic dermatitis decrease the compliance of patients and many women stop applying HRT. When transdermal gel was applied, the incidence of skin reactions was much lower and patient compliance was higher. From transdermal gel, the required amount of hormone rapidly penetrates the skin, then it accumulates in the outer corneated layer (the 'stratum corneum'), from where continuous absorption supplies the hormone levels required.

Currently marketed transdermal gels are estradiol containing monocomponent gels, therefore progestin should be replaced by an other route of administration in case of the majority of women (those with intact uterus) using these preparations, which results in adverse effects if oral treatment is applied.

Furthermore, the transdermal gels on the market are alcohol-based gels.

Gels for transdermal administration of steroids have been previously described in patents from which the most important ones are given in the list below. However all these gels differ from the liquid crystal gels according to the invention.

French Patent No. 2772270 comprises only estradiol for the treatment of postpartum depression. The gel contains carbomer, triethanolamine and large amounts of ethanol and water, about 45% and 50%, respectively.

U.S. Pat. No. 4,559,222 describes a transdermal composition containing only estradiol. The matrix applied contains mineral oil, polyisobutylene and colloidal silicon dioxide.

The European Patent Publication No. 371496 discloses a transdermal composition containing estradiol, oleic acid, linear alcohol lactate, dipropylene-glycol or m-pyrol (N-methyl-2-pyrrolidone).

The U.S. Pat. No. 4,956,171 discloses a transdermal system containing estradiol, sucrose cocoate and methyl laurate.

The Japanese Patent No. 2233621 discloses a gel containing estradiol and monocaprylic acid ester of glycolic acids.

The European Patent Publication No. 409383 discloses a transdermal composition. The estradiol containing gel comprises water-insoluble vinyl-pyrrolidone copolymer.

The European Patent Publication No. 137278 discloses a transdermal gel containing a steroid as active agent. Exemplatory steroid drugs include estradiol, levonorgestrel or gestodene. The gel matrix contains cross-linked silicon elastomer.

The GB patent No. 2158355 discloses a transdermal composition that can contain estradiol or levonorgestrel as active agents dispersed in a solvent mixture of propylene-glycol and glycerine.

The German Patent No. 3836862 discloses a transdermal composition containing a large amount of adhesive as well as fatty acid esters as absorption promoting agent. Steroid drugs include estradiol, levonorgestrel, gestodene and a combination thereof. The gel prepared in this way are applied for filling patches.

The European Patent Publication No. 367431 discloses a transdermal composition containing estradiol and a progestin. Steroids are delivered to skin in a mixture of 45-55% of isopropyl alcohol and isobutyl alcohol as well as in a gel containing water and methylcellulose.

The U.S. Pat. No. 5,019,395 discloses a transdermal composition containing a combination of estrdiol and progesteron as active agents as well as propylene-glycol diester of caprylic acid as solvent, coconut oil, ethanol and silicon dioxide as gelatinizing agent.

The European Patent Publication No. 587047 discloses a composition for HRT containing among others estradiol and gestodene or levonorgestrel, in combination as well. The gelatinizing agent is carboxyvinyl polymer.

The German Patent No. 4405898 discloses a composition for HRT among others containing estradiol and gestodene or levonorgestrel, also in combination. The gel contains dimethyl isosorbide.

The U.S. Pat. No. 5,453,279 discloses a composition for HRT among others containing estradiol and levonorgestrel, also in combination. The gel contains dialkyl citrate, decyl- or lauryl alcohol as well as propylene-glycol.

The Patent No. WO 9603119 discloses a composition for estrogen replacement therapy containing estradiol and levonorgestrel, also in combination. The gel contains acrylate as adhesive and linoleic acid.

The Patent No. WO 9630000 discloses a transdermal composition containing estradiol and norethindone acetate as active agents as well as ethylcellulose, isopropyl myristate and more than 70% of ethanol, which forms a flexible film on the skin after rapid evaporation.

The European Patent Publication No. 811381 discloses the formulation of a transdermal composition containing the mixture of estrogen and progestin. Estradiol is applied as estrogen component and primarily norethindone acetate but also progesterone, medroxyprogesterone and gestadene are applied as progestin component. The components of the gel are as follows: an aliphatic alcohol having 10 to 18 carbon atoms as absorption-promoting agent, a diethylene glycol monoalkyl ether, acrylic acid polymer or copolymer, triethanolamine, propylene-glycol as well as about 45% of ethanol and about 40% of water.

The World Patent Publication No. 9803156 discloses a local cosmetic hormone replacement composition containing a mixture of estrogen and progestin encapsulated in liposomes.

The German Patent No. 19701949 discloses a transdermal therapeutic system for hormone delivery among others with estradiol as active agent. The hydrogel contains the drug in a solid dispersion in combination with a structure-decomposing and a structure-forming additive.

The Patent No. WO 9920257 discloses a transdermal composition containing the mixture of estrogen and progesteron as active agents. The components of the gel are dioxolane- or dioxine-derivative or acetal as absorption promoter as well as propylene-glycol, 35-75% of ethanol, water and cellulose as thickening agent.

The U.S. Pat. No. 5,912,009 discloses a transdermal composition containing lauryl-glycolic acid in which estradiol is listed among active agents.

The French Patent No. 2774595 discloses a transdermal composition containing estradiol formed by the application of the mixture of an oil-in-water emulsion and an ether.

The French Patent 2777784 discloses a hormone replacement composition in which a progesteron suspension is formed in a solution prepared by dissolving estradiol in a lipophilic agent.

In the Patent No. WO 9962497 the composition disclosed is the mixture of an oily and an aqueous gel. Estradiol is dissolved in the oily gel, progesteron is dissolved in the aqueous gel and a cellulose polymer is added to the mixture of the gels.

The European Patent Publication No. 656213 describes a composition for estrogen replacement in postmenopause containing sodium-hyaluronate having a molecular mass from 150.000 to 225.000 and providing a higher than 10 mg dose with respect to a person of 70 kg body weight.

The application of transdermal gels is rare in the case of further active agents listed in the present invention. The closest prior arts are as follows:

The Patent No. WO 2003013482 discloses the application of a transdermal patch containing ondansetron in adhesive cross-linked copolymer.

The Patent No. WO 2000047208 discloses a transdermal patch containing ondanstron as active agent as well as 20-80% of alcohol, 1-50% of a fatty acid derivative and 15-80% of water.

The Hungarian Patent No. 207795 discloses a topical gel composition containing metronidazole as active ingredient and gelatinizing agents such as celluloses or acrylic acid polymers, and buffered between the pH of 3.0 and 4.25.

The Canadian Patent No. 2423836 discloses a transdermal composition containing fentanyl as active agent with acrylate copolymer.

The Canadian Patent No. 1325381 discloses a transdermal composition of laminated structure containing fentanyl as active agent.

The German Patent No. 10141650 discloses a transdermal patch containing fentanyl as active agents.

The European Patent Publication No. 710491 discloses a subdermal implantation containing nestorone as active agent.

The U.S. Pat. No. 6,238,284 discloses a transdermal patch containing norethisterone as active ingredient.

The European Patent Publication No. 1197212 discloses a percutaneous absorptive adhesive composition containing norethisterone with styrene-isoprene-styrene copolymer.

The Japanese Patent No. 7267860 discloses a transdermal composition, patch, ointment and cream containing eperisone and tolperisone as active agents.

The Japanese Patent Publication No. 6211696 discloses a percutaneous absorptive composition containing eperisone and tolperisone as active agents with di- and tricarboxylic acid or cross-linked polyvinylpyrrolidone.

The European Patent Publication No. 454089 discloses a percutaneous composition containing eperisone and tolperisone as active agents with cross-linked polyvinylpyrrolidone.

The European Patent Publication No. 295411 discloses a percutane composition containing eperisone and tolperisone as active agents with the monoglyceride of an aliphatic acid and/or an ester of a lactic acid.

The US Patent No. 2002028789 discloses a topical cream composition containing ketamine as active agent.

The new hyaluronic acid zinc associate (complex) in the World Patent Publication No. 9010020 obtained protection for medicinal and cosmetic applications, among others in the form of gel, cream or ointment.

Marketed and prior art gel pharmaceutical compositions have several disadvantages.

Such a disadvantage is the high alcohol and/or organic solvent content that causes skin irritation. The known transdermal systems containing active agents, which are sparingly soluble or insoluble in water comprise a considerable amount of organic solvent. The ratio of the organic phase is higher than 45% in the complete gel and occasionally it may be as high as 70 or even 75%. There is such a preparation that contains 45-55% of polyvalent alcohols (isopropyl alcohol, isobutyl alcohol) as organic solvents.

Another disadvantage relates to the aesthetic features of the formulations. There are products that are not transparent in consequence of the additives applied. These kinds of additives involve colloidal silicon dioxide which is applied as viscosity-increasing agent or methylcellulose that swells readily in water but gives a slightly opalescent formulation.

Suspension formulations with undissolved active agents may become inhomogeneous due to the inhomogeity of the active agent particles.

Incomplete dissolution of the active agent from the gel formulation is another important problem. Polymeric matrices may impede dissolution and give rise to this undesirable phenomenon. Certain frame-forming materials like carboxyvinyl polymer or different cellulose-based polymers form a film after the evaporation of the solvent, however transdermal absorption of the active agent from this film-layer is a process of hindered diffusion.

Finally, lipogels that are often used to facilitate dissolution of active agents with poor aqueous solubility are also disadvantageous. The unfavourable feature of lipogels is that by smearing them onto the skin, they give rise to an oily-greasy sensation, since they cover and plug skin pores they impede normal skin respiration. The materials with such an effect include silicon oils, oleic acid derivatives but also glycerol, which is felt sticky rather than greasy.

With the aim of solving the above-listed problems we have developed a new, modern transdermal gel pharmaceutical composition, which has never occurred in prior art.

Our aim was also to develop a transdermal gel -pharmaceutical composition that is suitable for hormone replacement therapy and not only as an estradiol-containing monogel but also as a two-component preparation, which in combination with estrogen also contains a progestin component offering favourable effects while being free from androgenic effects.

Furthermore, it was also our aim to develop transdermal gel pharmaceutical compositions not known in prior art with active agents including among others ondansetron, terbinafine, fluconazole, metronidazole, fentanyl, nandrolone decanoate, nestorone, norethisterone, eperisone, tolperisone, vinpocetine, ketamine, vincristine and vinblastine.

Through experimentation we have been able to produce a liquid crystal gel having a composition not mentioned in prior art, for use in the manufacture of new pharmaceutical compositions and healing cosmetics containing one or more active agents.

The invention relates to a liquid crystal gel for use in the manufacture of transdermal pharmaceutical compositions and healing cosmetics and where the gel contains polyoxyethylene-glyceryl-trioleate, propylene-glycol, isopropyl myristate and a hyaluronic acid salt or complex.

The invention also relates to transdermal pharmaceutical composition consists of an estrogen and a progestin component as well as a liquid crystal gel containing polyoxyethylene-glyceryl-trioleate, propylene-glycol, isopropyl myristate and a hyaluronic acid salt or complex.

The invention also relates to method of treatment for transdermal hormone replacement therapy, where a pharmaceutical composition consists of an estrogen and a progestin component as well as a liquid crystal gel containing polyoxyethylene-glyceryl-trioleate, propylene-glycol, isopropyl myristate and a hyaluronic acid salt or complex is applied onto the surface to be treated.

The invention also relates to transdermal pharmaceutical composition consists of one or more active agents (among others, ondansetron, terbinafine, fluconazole, metronidazole, fentanyl, nandrolone decanoate, nestorone, norethisterone, eperisone, tolperisone, vinpocetine, ketamine, vincristine, vinblastine) as well as a liquid crystal gel containing polyoxyethylene-glyceryl-trioleate, propylene-glycol, isopropyl myristate and a hyaluronic acid salt or complex.

The invention also relates to method of treatment for transdermal therapies, where a pharmaceutical composition consists of one or more active agent components (among others, ondansetron, terbinafine, fluconazole, metronidazole, fentanyl, nandrolone decanoate, nestorone, norethisterone, eperisone, tolperisone, vinpocetine, ketamine, vincristine, vinblastine) as well as a liquid crystal gel containing polyoxyethylene-glyceryl-trioleate, propylene-glycol, isopropyl myristate and a hyaluronic acid salt or complex is applied onto the surface to be treated.

The detailed description of the invention is given below.

In order to facilitate understanding the following definitions are provided:

The name of the surfactant polyoxyethylene-glycerol-trioleate we used further as "Tagat TO V".

"Room temperature" refers to a temperature value between 20 and 25° C.

The abbreviation, "HRT" stands for hormone replacement therapy.

"First-pass metabolism" is a commonly used term in the medical practice to denote the intensive metabolism of an orally administered active agent reaching the liver through the portal vein after absorption from the gastrointestinal tract.

The figures attached illustrate the followings:

FIG. 1 depicts the ternary phase diagram indicating the concentration range required for each component to form liquid crystal regions in the liquid crystal transdermal gel pharmaceutical composition. One side of the triangle indicates the concentration of the surfactant phase, the other side that of the oily phase, while the third side shows the percentile amount of the aqueous phase.

Figure 2:
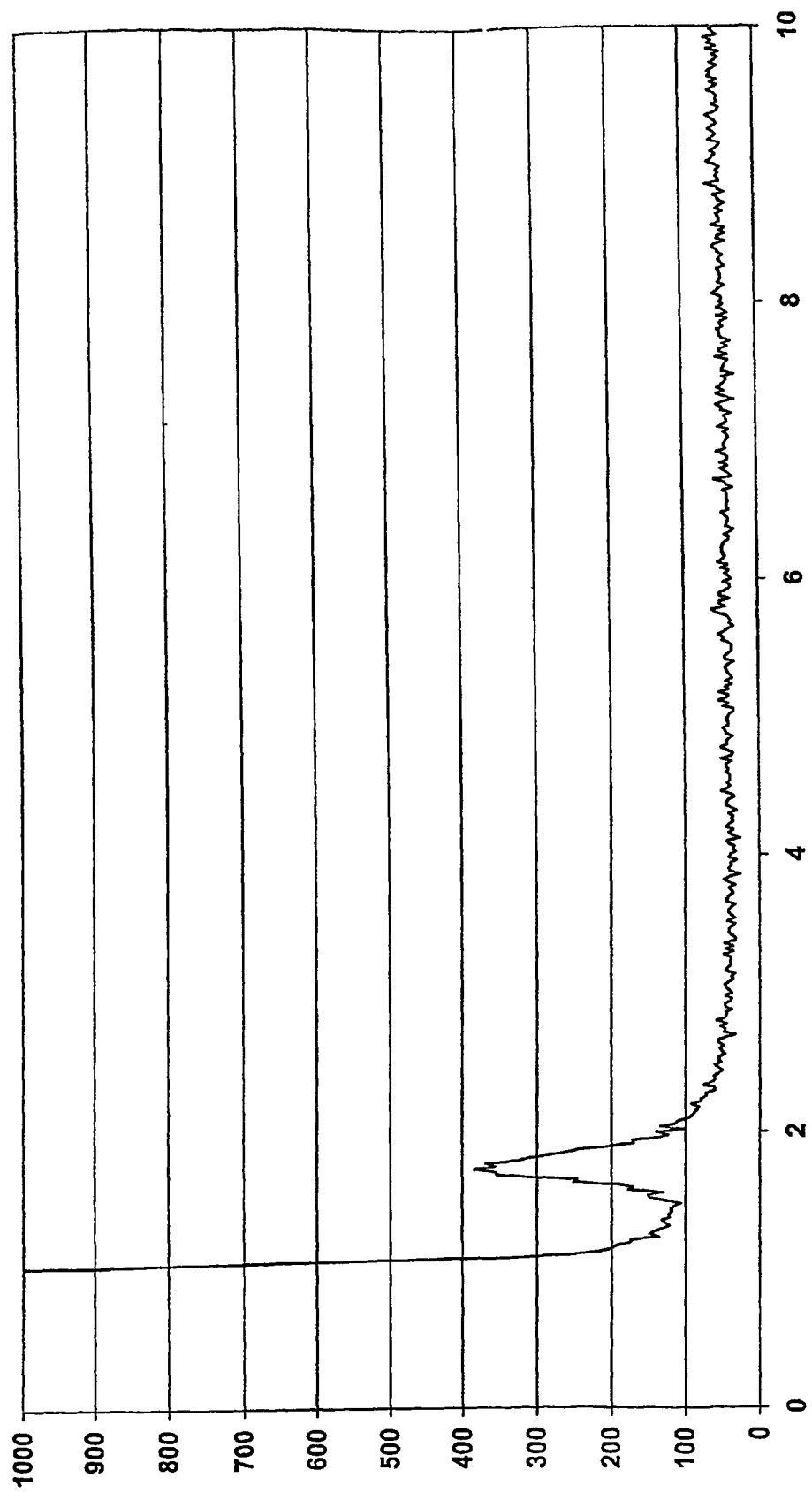

FIG. 2 demonstrates the X-ray diffraction pattern of a gel sample not containing hyaluronic acid salt or complex. The x-axis measures the diffractional 2θ angle (°), while the y-axis indicates peak intensity per second values.

Figure 3:
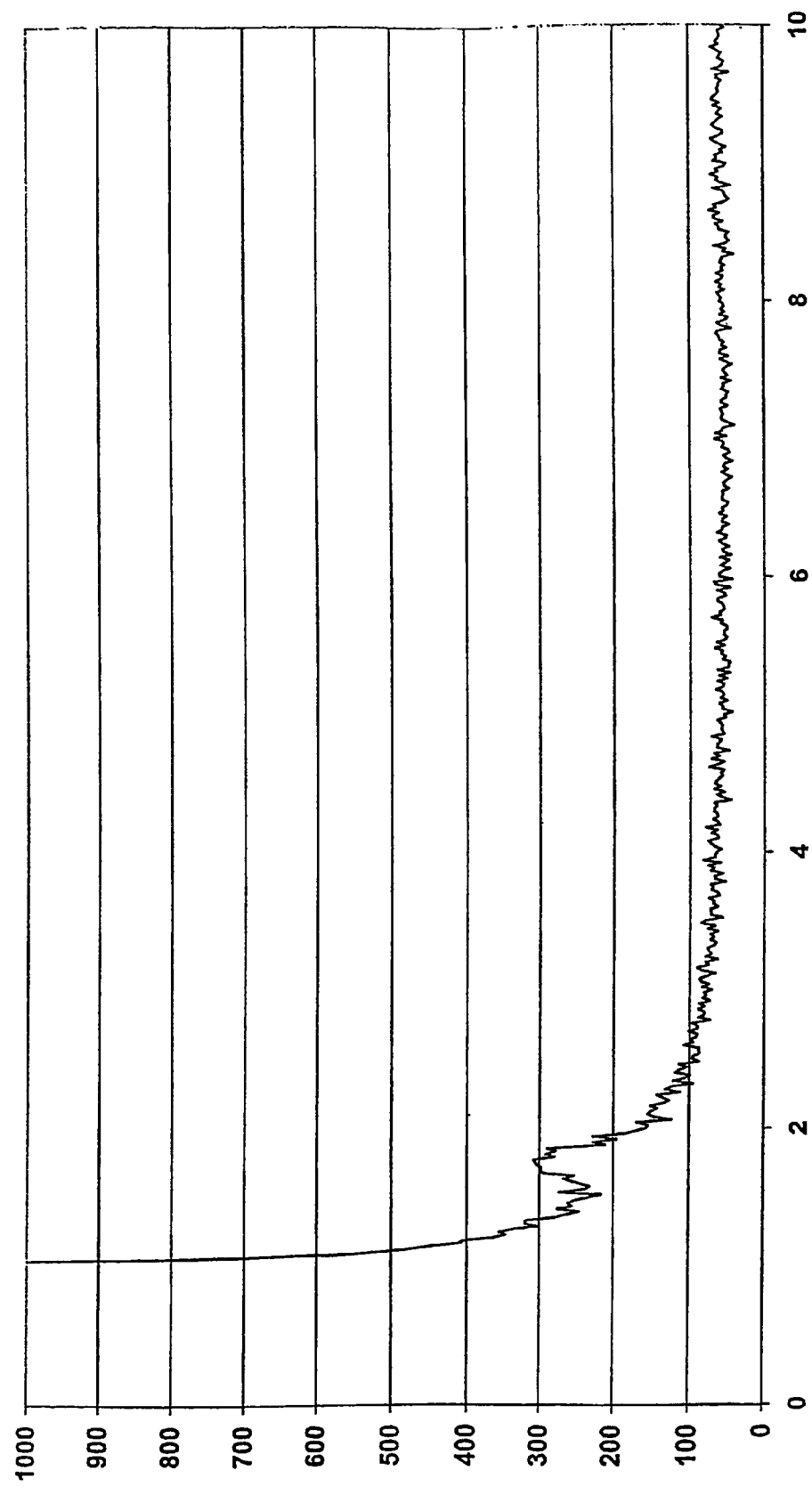

FIG. 3 demonstrates the X-ray diffraction pattern of a gel sample containing a hyaluronic acid-zinc complex. The x-axis measures the diffractional 2θ angle (°), while the y-axis indicates peak intensity per second values.

Figure 4:
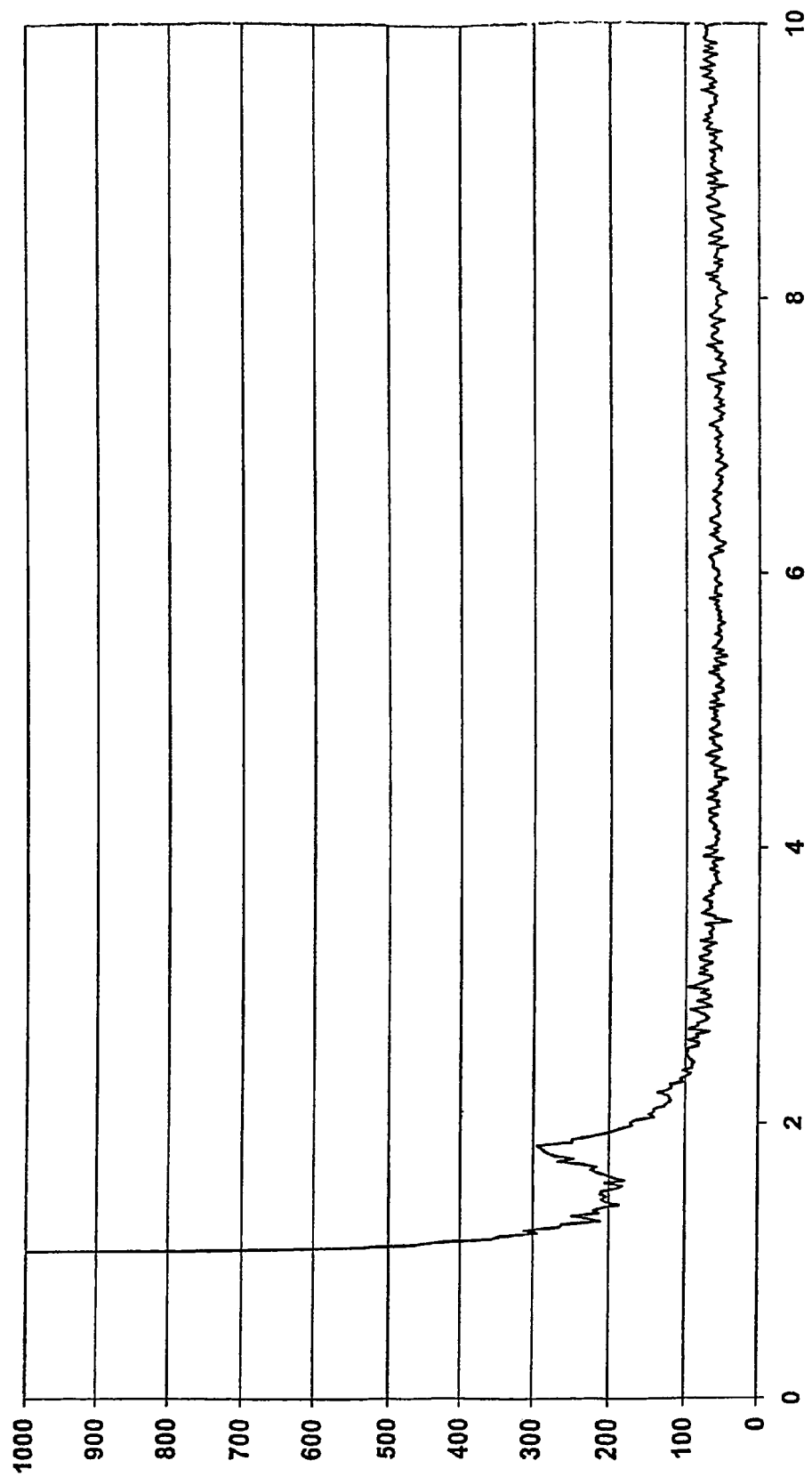

FIG. 4 demonstrates the X-ray diffraction pattern of a gel sample containing a high molecular weight sodium-hyaluronate. The x-axis measures the diffractional 2θ angle (°), while the y-axis indicates peak intensity per second values.

Figure 5:
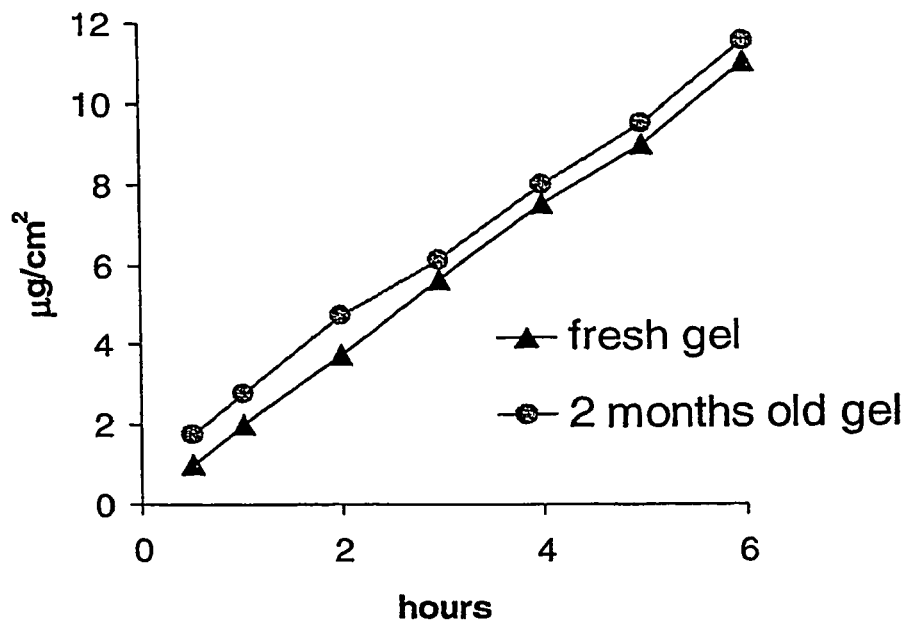

FIG. 5 demonstrates in a Hanson's cell study the release of estradiol from and the stability of estradiol in a fresh and a 2 months old gel sample containing estradiol and etonogestrel as active agents. The x-axis indicates the sampling times in hours, while the y-axis measures the amount of released estradiol in $\mu g/cm^2$ units.

Figure 6:
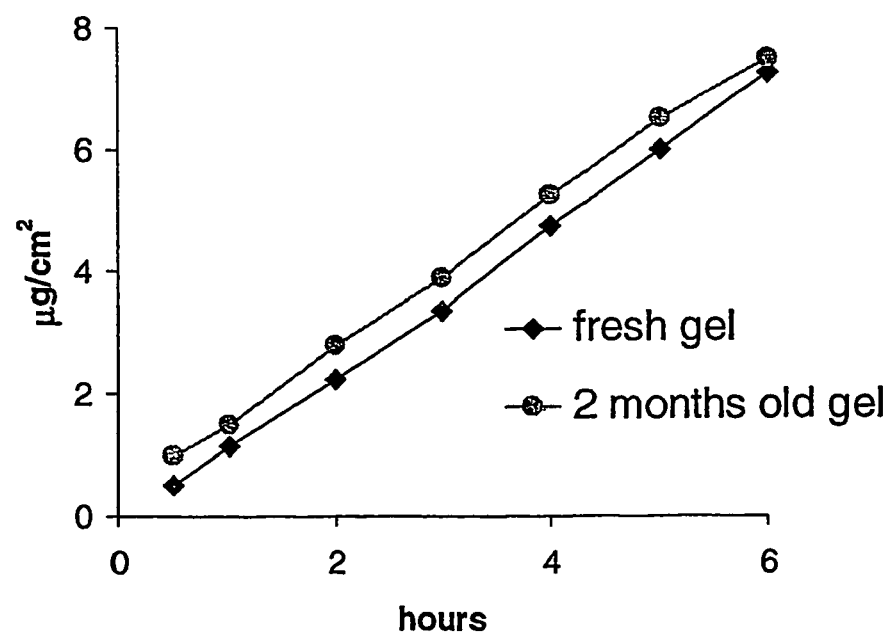

FIG. 6 demonstrates in a Hanson's cell study the release of etonogestrel from and the stability of etonogestrel in a fresh and a 2 months old gel sample containing estradiol and etonogestrel as active agents. The x-axis indicates the sampling times in hours, while the y-axis measures the amount of released etonogestrel in $\mu g/cm^2$ units.

Figure 7:
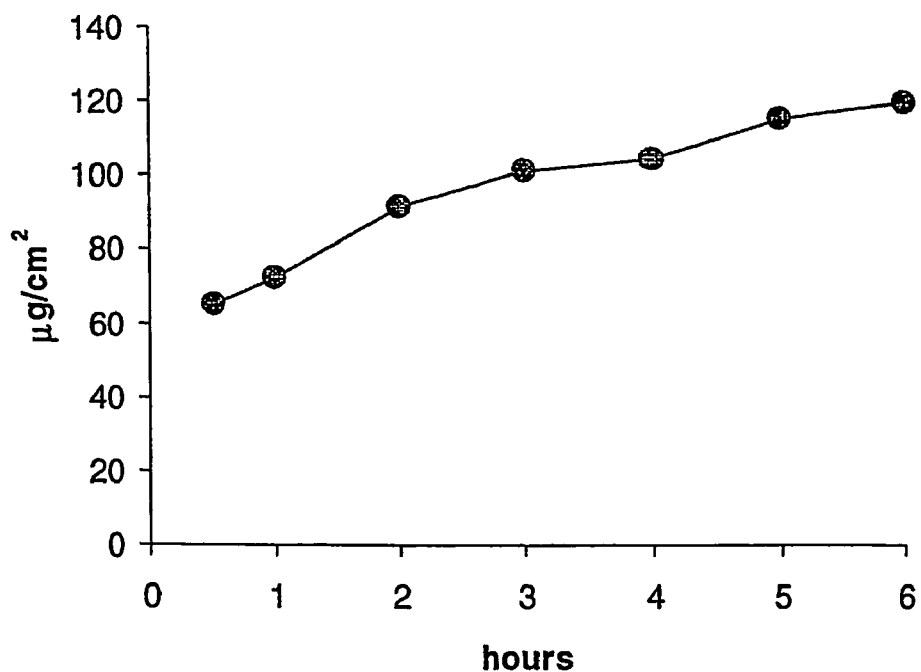

FIG. 7 demonstrates in a Hanson's cell study on hydrophilic membrane the release of ondansetron from a fresh gel sample containing ondansetron as active agent. The x-axis indicates the sampling times in hours, while the y-axis measures the amount of released ondansetron in $\mu g/cm^2$ units.

Figure 8:
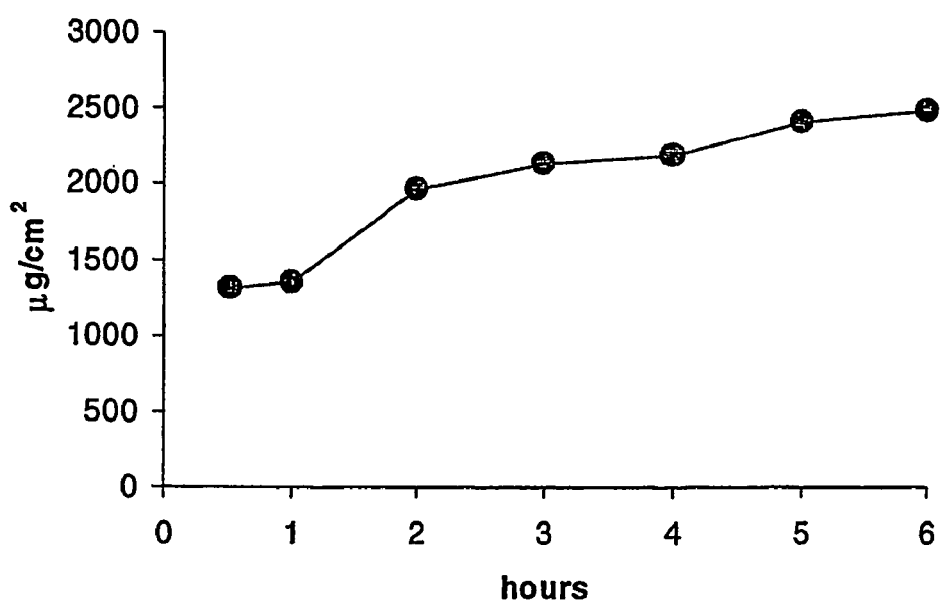

FIG. 8 demonstrates in a Hanson's cell study on hydrophilic membrane the release of terbinafine from a fresh gel sample containing terbinafine as active agent. The x-axis indicates the sampling times in hours, while the y-axis measures the amount of released terbinafine in $\mu g/cm^2$ units.

Figure 9:
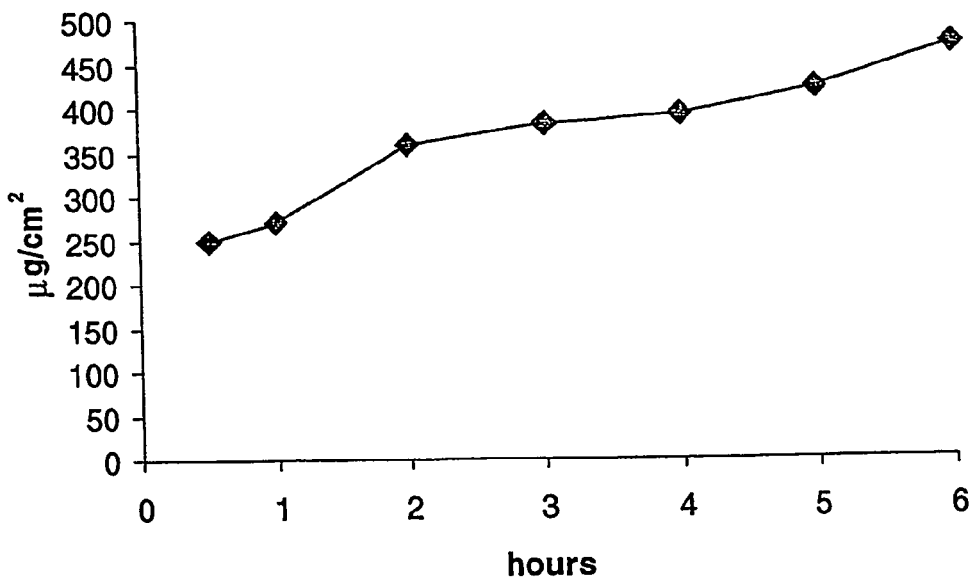

FIG. 9 demonstrates in a Hanson's cell study on hydrophilic membrane the release of metronidazole from a fresh gel sample containing metronidazole as active agent. The x-axis indicates the sampling times in hours, while the y-axis measures the amount of released metronidazole in $\mu g/cm^2$ units.

Figure 10:
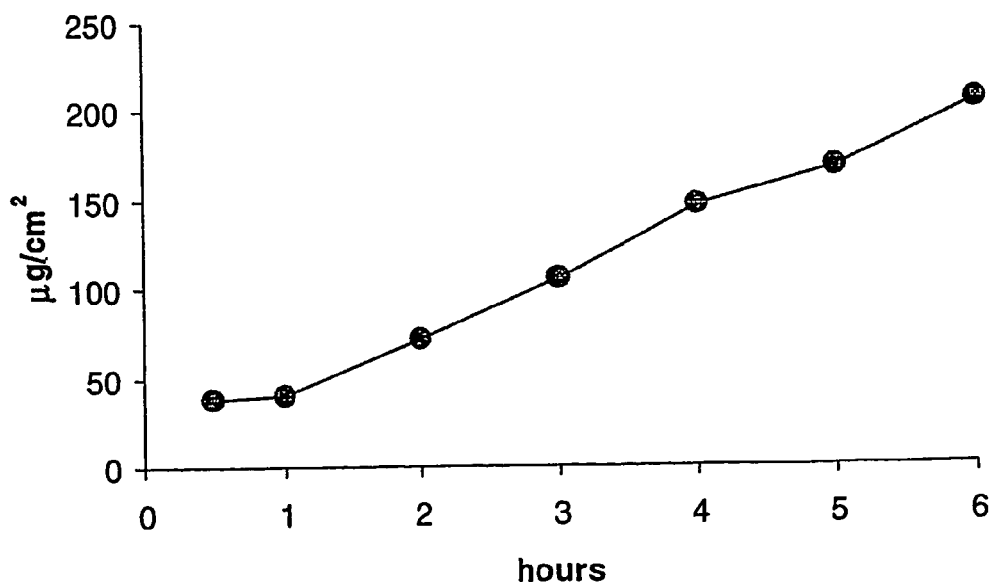

FIG. 10 demonstrates in a Hanson's cell study on lipophilic membrane the release of metronidazole from a fresh gel sample containing metronidazole as active agent. The x-axis indicates the sampling times in hours, while the y-axis measures the amount of released metronidazole in $\mu g/cm^2$ units.

Figure 11:
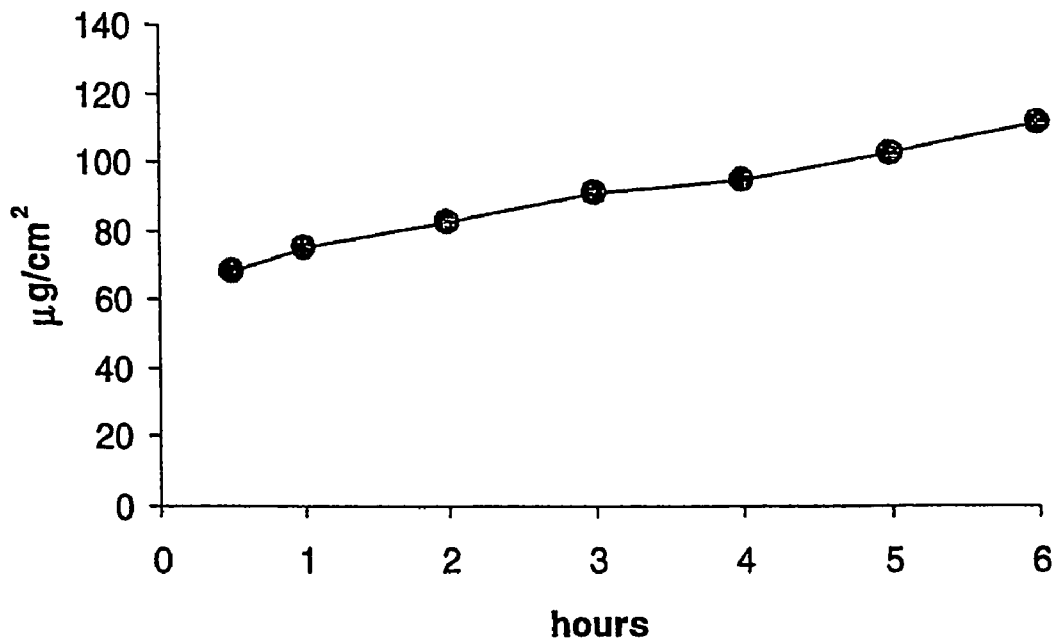

FIG. 11 demonstrates in a Hanson's cell study on hydrophilic membrane the release of eperisone from a fresh gel sample containing eperisone as active agent. The x-axis indicates the sampling times in hours, while the y-axis measures the amount of released eperisone in $\mu g/cm^2$ units.

Figure 12:
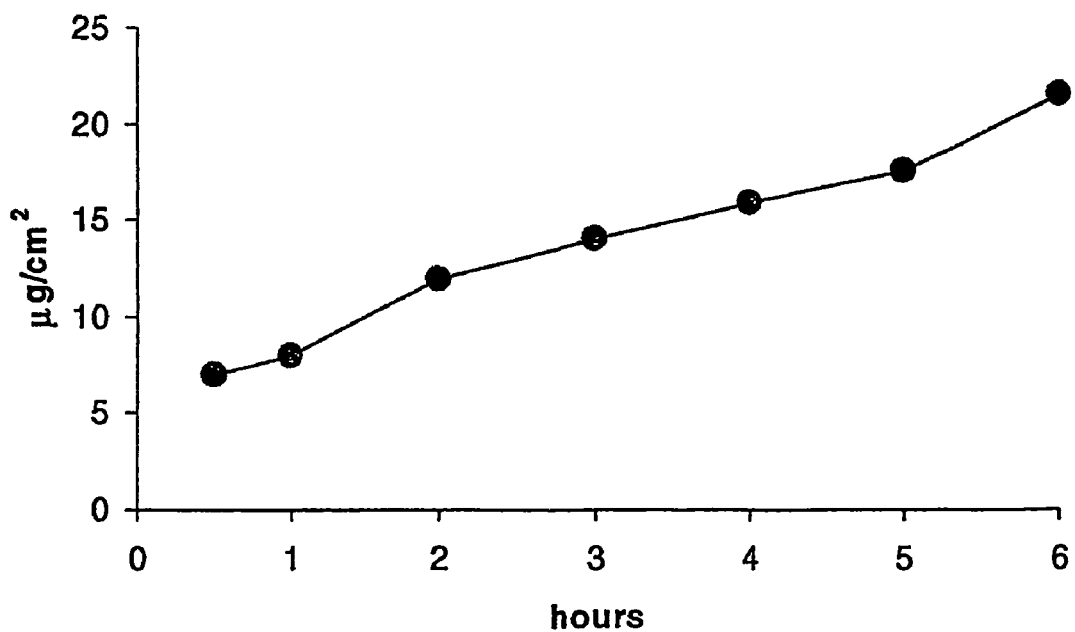

FIG. 12 demonstrates in a Hanson's cell study on lipophilic membrane the release of eperisone from a fresh gel sample containing eperisone as active agent. The x-axis indicates the sampling times in hours, while the y-axis measures the amount of released eperisone in $\mu g/cm^2$ units.

Figure 13:
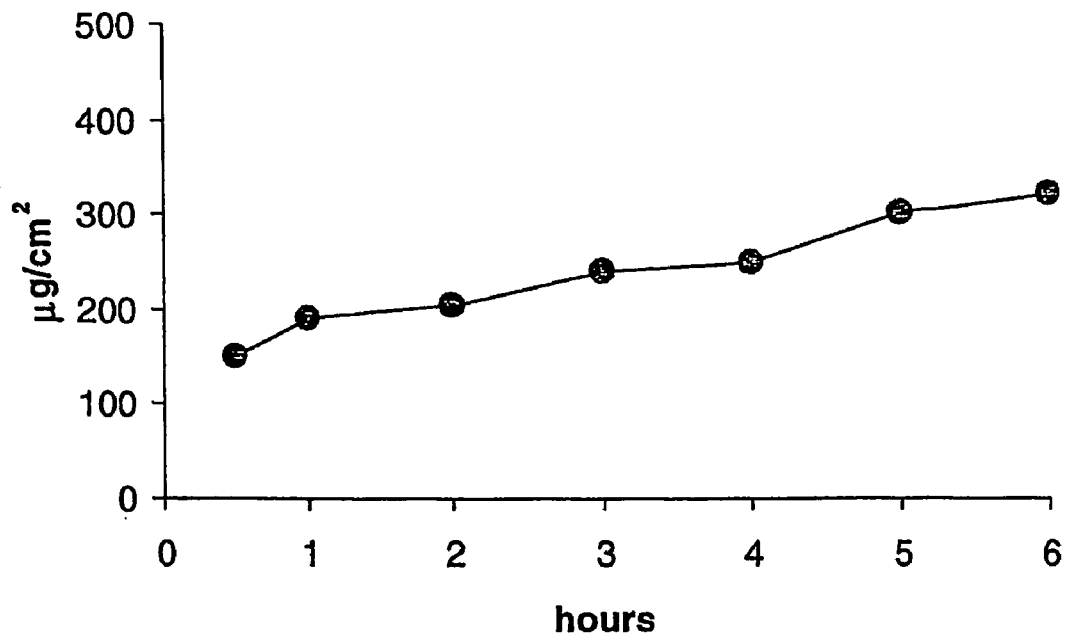

FIG. 13 demonstrates in a Hanson's cell study on hydrophilic membrane the release of tolperisone from a fresh gel sample containing tolperisone as active agent. The x-axis indicates the sampling times in hours, while the y-axis measures the amount of released tolperisone in $\mu g/cm^2$ units.

Figure 14:
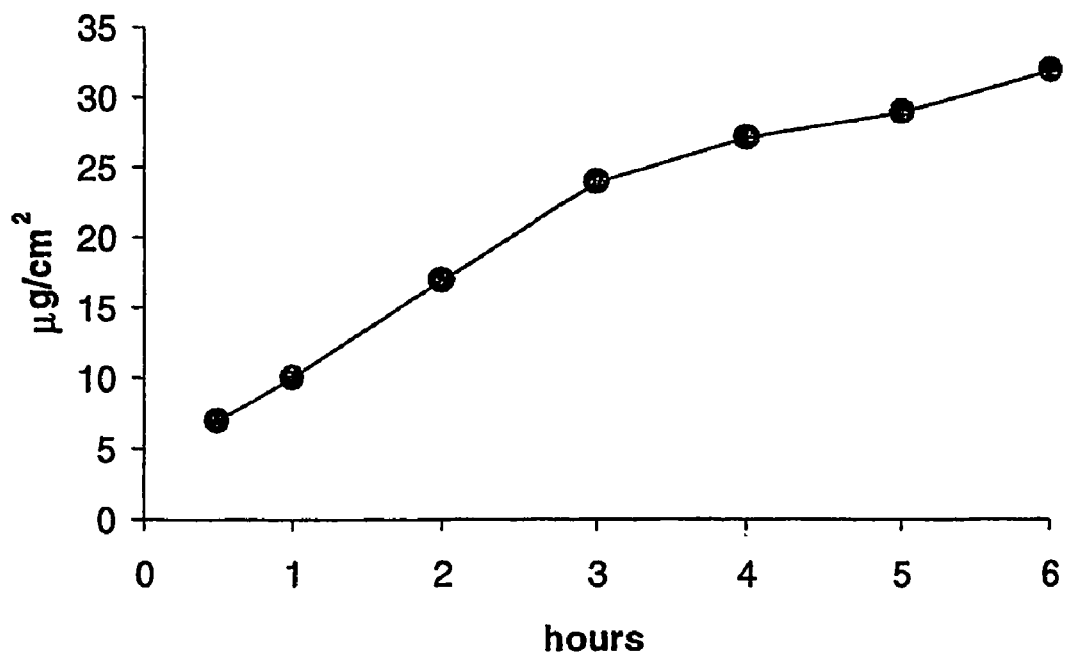

FIG. 14 demonstrates in a Hanson's cell study on lipophilic membrane the release of tolperisone from a fresh gel sample containing tolperisone as active agent. The x-axis indicates the sampling times in hours, while the y-axis measures the amount of released tolperisone in $\mu g/cm^2$ units.

The invention relates to a liquid crystal gel containing Tagat TO V, propylene-glycol, isopropyl myristate and a hyaluronic acid salt or complex for use in the manufacture of pharmaceutical compositions and healing cosmetics.

The results of our experiments on the gel-formation of different compositions led to the surprising finding that using a specific concentration range for each component we have found a new liquid crystal gel not known in prior art.

The liquid crystal transdermal gel according to the present invention consists of surfactants and an oil phase and an aqueous phase. In addition, the structure of the gel developed is a microemulsion gel containing a hyaluronic acid salt or complex, a macromolecule that is a normal component of the skin. From the aspects of colloid chemistry, the structure of the gel according to the present invention is at the same time a microemulsion, a liquid crystal and colloid system containing a hyaluronic acid salt or complex. The complex gel system forming this way has never been applied to transdermal drug administration.

The liquid crystal transdermal gel according to the present invention is composed of the following components:

As surfactant, we have used Tagat TO V i.e. polyoxyethylene-glyceryl-trioleate which is a surfactant of vegetable origin (manufacturer: Goldschmidt AG.). The amount of Tagat TO V in the gel varies between 26.7 and 40% of the total weight of the gel, preferably between 30 and 35% (w/w) and most preferably it is 33.3% (w/w).

Beside the surfactant, propylene-glycol is applied as a cosurfactant. The amount of propylene-glycol added to the gel varies between 13.3 and 20% of the total weight of the gel, preferably between 15 and 18% (w/w) and most preferably it is 16.7% (w/w).

In the liquid crystal transdermal gel according to the present invention the ratio of the surfactant, Tagat TO V and the cosurfactant, propylene-glycol is always 2:1.

The oil phase of the gel consists of isopropyl myristate. The amount of isopropyl myristate added to the gel varies between 5 and 35% of the total weight of the gel, preferably between 17 and 20% (w/w) and most preferably it is 19% (w/w).

In the liquid crystal transdermal gel according to the present invention the aqueous phase means the mixture of water, ethanol, benzyl alcohol and a hyaluronic acid salt or complex (preferably sodium-hyaluronate or hyaluronic acid zinc complex).

The amount of water added to the gel varies between 12.5 and 26.5% of the total weight of the gel, preferably between 20 and 25% (w/w) and most preferably it is 24.9% 30 (w/w).

Ethanol is required to homogenously disperse the active agents of poor aqueous solubility in the gel. The amount of ethanol in the gel according to the present invention varies between 0.01 and 10% of the total weight of the gel, preferably between 4 and 6% (w/w) and most preferably it is 5% (w/w), accordingly ethanol is used in lower proportion in the gel according to the present invention than in the transdermal gel compositions available on the market.

The water: ethanol ratio in the aqueous phase may vary from 5:1 to 3:1.

Benzyl alcohol is used as preservative, its amount varies between 0.5 and 1.5% of the total weight of the gel, preferably between 0.7 and 1.3% (w/w) and most preferably it is 1.0% (w/w).

The liquid crystal transdermal gel according to the present invention also contains a hyaluronic acid salt or complex. Sodium hyaluronate is the preferred hylauronic acid salt and for the purpose of the present invention fractions with the mean molecular weight of 580,000-620,000 and 1,350,000-1,400,000 are used. Hyaluronic acid zinc complex is the preferred hylauronic acid complex and for the purpose of the present invention fraction with the mean molecular weight of 600,000-650,000 is used. The amount of sodium hyaluronate and hyaluronic acid zinc complex in the gel varies between 0.01 and 2% of the total weight of the gel, preferably between 0.05 and 0.15% (w/w) and most preferably it is 0.1% (w/w).

It is important to emphasize that the formation of the liquid crystal transdermal gel according to the present invention cannot take place unless within the well defined concentration ranges of the listed components.

The advantages of transdermal pharmaceutical compositions and healing cosmetics based on the liquid crystal gel according to the present invention are the followings:

Advantages Arising from the Oil/Water Type Microemulsion:
An oil/water type microemulsion is formed. Oil is present as a colloid dispersion, whereby the dissolution rate of active agents being soluble in non-polar medium increases, thus microemulsion allows the preparation of a solution formulation in the majority of the cases. It is well known that the active agent needs to be dissolved in order to disperse it in the gel homogenously and that homogenous dispersion of a suspension type active agent is unreliable. The above ones are associated with an important biopharmaceutical advantage: the diffusion of the oil soluble agents takes place on an extremely large surface that ensures an extremely rapid drug release.

The composition produced this way is transparent and has a favourable aesthetic appearance. Beside the aesthetic aspects, transparency also offers the advantage that any alteration (degradation) can be detected macroscopically by visual inspection.

The composition produced this way is stable thermodynamically. (Macroemulsions and creams are not thermodynamically stable, they are characterized by kinetic stability only.)

Advantages Arising from Liquid Crystal Structure:
Liquid crystal structure endows the system with higher rigidity, wherefore the composition is not fluidic but—depending on the level of orderliness—plastic or somewhat viscoelastic. Dosing is much more easy with the systems having such rheological properties than with fluids. The distribution of liquid crystal gels over the selected skin area is much more easy and accurate than that of any liquid formulation.

The liquid crystal character is the result of the ordered structure of surfactants. The appreciable amount of surfactants has the following advantages:
a/ It is a good wetting agent for insoluble, suspended active agent (present in solid particles), whereby it increases the rate of dissolution.
b/ The composition is readily and quickly absorbed into the skin, thus it is free from leaving greasy spots or other unpleasant residues.
c/ Surfactants are generally known for their penetration-enhancing effects, accordingly the surfactant promotes the penetration through the biological membranes of those active agents, which in the absence of the surfactant could not traverse the cellular wall. The active agents incorporated into the compositions according to the present invention can readily penetrate into the outer layers of the skin, into the non-polar stratum corneum, but they show a poor penetration into the highly aqueous living epidermis. Surfactants are able to increase significantly this latter penetration, i.e. the penetration into the epidermis.

Advantages Provided by the Colloid System Containing a Water Soluble Hyaluronic Acid Salt or Complex:
Being related to natural skin constituents, hyaluronic acid salt or complex offers the advantage of increasing the viscosity of the composition thus the precision of its the dosage and distribution.

Hyaluronic acid salt or complex also promotes the wetting of the active agents that are poorly soluble in water and semi-polar media.

Biopolymers (natural macromolecular constituents of living organisms) are generally known for their penetration-enhancing effects, too.

In conclusion, the transdermal pharmaceutical compositions and healing cosmetics based on the liquid crystal gel according to the present invention have complex physico-chemical, pharmaceutical technology and biopharmaceutical advantages. On the basis of above advantages, the compositions according to the present invention are clearly superior to any traditional vehicles (such as macroemulsions, creams and polymeric gels).

We have determined the concentration range required for each component to form liquid crystal regions in the liquid crystal transdermal gel pharmaceutical composition, which are shown in the ternary phase diagram in FIG. 1. Each apex of the triangle represents the 100% proportion of the component indicated at the apex, whereas the side opposite to any apex represents 0% proportion of the given component. One side of the triangle indicates the concentration of the 2:1 mixture of surfactant and the cosurfactant, Tagat TO V and propylene-glycol, the second side indicates the oil phase, (isopropyl myristate in our case), while the third side indicates the proportion of the aqueous phase, in our case water, ethanol, benzyl alcohol and a hyaluronic acid salt or complex (preferably sodium hyaluronate or hyaluronic acid zinc complex). The water:ethanol ratio in the aqueous phase may vary from 5:1 to 3:1. The concentrations of the three components of the gel according to the present invention requires can be read from the diagram. Accordingly, the formation of the liquid crystal transdermal gel according to the present invention requires the following concentration ratios of the components indicated in the diagram:

| | |
|---|---|
| Tagat TO V surfactant and propylene-glycol co-surfactant (2:1) = | 40-60% |
| Isopropyl myristate = | 5-35% |
| Aqueous phase = | 25-40% |

(where the aqueous phase is a mixture of a colloidal solution of hyaluronic acid salt or complex and ethanol and benzyl alcohol)

The components of the liquid crystal transdermal gel according to the present invention have the following concentration ranges:

| | |
|---|---:|
| Tagat TO V | 26.7-40.0% |
| Propylene-glycol | 13.3-20.0% |
| Isopropyl myristate | 5.0-35.0% |
| Ethanol | 0.01-10.0% |
| Benzyl alcohol | 0.5-1.5% |
| Sodium-hyaluronate | 0.01-2.00% |
| Purified water | 12.5-26.5% |
| or | |
| Tagat TO V | 26.7-40.0% |
| Propylene-glycol | 13.3-20.0% |
| Isopropyl myristate | 5.0-35.0% |
| Ethanol | 0.01-10.0% |
| Benzyl alcohol | 0.5-1.5% |
| Hyaluronic acid zinc complex | 0.01-2.00% |
| Purified water | 12.5-26.5% |

The components of the liquid crystal transdermal gel according to the present invention preferably have the following concentration ranges:

| | |
|---|---:|
| Tagat TO V | 30.0-35.0% |
| Propylene-glycol | 15.0-18.0% |
| Isopropyl myristate | 17.0-20.0% |
| Ethanol | 4.0-6.0% |
| Benzyl alcohol | 0.7-1.3% |
| Sodium-hyaluronate | 0.05-0.15% |
| Purified water | 20.0-25.0% |
| or | |
| Tagat TO V | 30.0-35.0% |
| Propylene-glycol | 15.0-18.0% |
| Isopropyl myristate | 17.0-20.0% |
| Ethanol | 4.0-6.0% |
| Benzyl alcohol | 0.7-1.3% |
| Hyaluronic acid zinc complex | 0.05-0.15% |
| Purified water | 20.0-25.0% |

The components of the liquid crystal transdermal gel according to the present invention most preferably have the following concentration ranges:

| | |
|---|---:|
| Tagat TO V | 33.30% |
| Propylene-glycol | 16.70% |
| Isopropyl myristate | 19.00% |
| Ethanol | 5.00% |
| Benzyl alcohol | 1.00% |
| Sodium-hyaluronate | 0.1% |
| Supplemented with purified water ad | 100.0% |
| or | |
| Tagat TO V | 33.30% |
| Propylene-glycol | 16.70% |
| Isopropyl myristate | 19.00% |
| Ethanol | 5.00% |
| Benzyl alcohol | 1.00% |
| Hyaluronic acid zinc complex | 0.1% |
| Supplemented with purified water ad | 100.0% |

The liquid crystal transdermal gel according to the present invention is produced by mixing Tagat TO V, propylene-glycol and benzyl alcohol at room temperature then the mixture is homogenized preferably at less than 1500 r.p.m. for 5 minutes in a way that ensures the system remains free of air as far as possible. Non-aerated conditions can be ensured both by low stirring speed and preferably by the application of vacuum. The order the components are mixed can be changed.

The active agents (such as estrogen and progestin components) are dissolved in ethanol (or in aqueous ethanol in the case of other active agents provided their solubility allows) under continuous stirring.

The active agent solution is added to the mixture of Tagat TO V, propylene-glycol and benzyl alcohol and the mixture is homogenized by stirring at less than 1500 r.p.m. for at least 30 minutes.

To the mixture containing the active agent solution as well as the mixture of Tagat TO V, propylene-glycol and benzyl alcohol, isopropyl myristate is added and the mixture is homogenized by stirring at less than 1500 r.p.m. for at least 30 minutes.

Parallel to the above process, an aqueous solution is made of sodium-hyaluronate or hyaluronic acid zinc complex by the use of a mixer working preferably at less than 1500 r.p.m. The solution obtained this way is a highly viscous, thick fluid. After complete swelling is attained—which takes a minimum of 1 hour, but may take as much as 4 hours depending on the performance of the mixer—the aqueous solution of sodium-hyaluronate or hyaluronic acid zinc complex is admixed to the above mixture and the mixture obtained is made up to volume with purified water. The system composed this way is homogenized with a stirrer working preferably at less than 1500 r.p.m. to allow the formation of the gel structure. The duration of homogenization is at least 30 minutes.

The viscosity of the gel system produced this way is monitored using a Brookfield type viscosimeter at grade 2.5. The consistency of the gel is satisfactory if its viscosity falls in the range of 1000-15000 cPs.

Liquid crystals are identified by the means of a Leica image analyzer (Leica Q500MC Image Processing and Analysis System) in a polarization light microscopy study.

For the verification of the liquid crystal structure of the transdermal gel according to the present invention an X-ray diffraction analysis was made, which provided the interlamellar repeated distance between lamellar liquid crystal domains.

The X-ray diffraction analysis of the gel was carried out as follows: The samples stored for one week were put into a copper sample holder and covered with Mylar-foil. The analysis was made by the means of a Phillips PW 1820 diffractometer the copper $K_{\alpha 1}$ radiation source of which worked at the wavelength of $\lambda = 1.54$ nm. The source was operated at a voltage of 40 kV and a current of 35 mA, and a solid particle detector was applied. The incident beam reached the sample through an automatic divergence slit and a monochromator. The goniometer operated at a speed of $0.05°$ $2\theta$/second, with a -step width of $0.02°$ $2\theta$. The sample was scanned between $1°$ and $10°$ $2\theta$ values. The analysis was made at room temperature.

The position and intensity of the most characteristic peaks were determined by the second order derivation peak evaluation method.

The interlamellar repeated distances characterising the extent of orderliness in a liquid crystal were calculated by the Bragg's equation:

$$\lambda = 2d \sin \theta \text{ where}$$

$\lambda$: wavelength (nm),
d: interlamellar repeated distance (mn),
$2\theta$: diffraction angle (degrees).

Altogether three types of samples were subjected to X-ray diffraction analysis: gel without hyaluronic acid (sample 1), gel containing hyaluronic acid zinc complex (sample 2) and gels containing high molecular weight (average molecular weight of 1,350,000-1,400,000 sodium-hyaluronate (sample 3) having the exact composition as follows:

| Sample 1: | |
|---|---|
| Tagat TO V | 33.30% |
| Propylene-glycol | 16.70% |
| Isopropyl myristate | 19.00% |
| Ethanol | 5.00% |
| Benzyl alcohol | 1.00% |
| Supplemented with purified water ad | 100.0% |

| Sample 2: | |
|---|---|
| Tagat TO V | 33.30% |
| Propylene-glycol | 16.70% |
| Isopropyl myristate | 19.00% |
| Ethanol | 5.00% |
| Benzyl alcohol | 1.00% |
| Hyaluronic acid zinc complex | 0.10% |
| Supplemented with purified water ad | 100.0% |

| Sample 3: | |
|---|---|
| Tagat TO V | 33.30% |
| Propylene-glycol | 16.70% |
| Isopropyl myristate | 19.00% |
| Ethanol | 5.00% |
| Benzyl alcohol | 1.00% |
| Sodium-hyaluronate (high molecular weight) | 0.10% |
| Supplemented with purified water ad | 100.0% |

FIGS. 2, 3 and 4 depict the X-ray diffraction pattern of gel samples 1, 2 and 3, respectively. The abscissa measures the diffraction 2θ angle (°), while the ordinate indicates peak intensity per second values.

For gel sample 1 the interlamellar repeated distance determined by X-ray diffraction was 50.75 Å, for sample 2 it was 51.02 Å, while for sample 3 it was 49.13 Å. On the basis of the results of the X-ray diffraction analyses of three sample types it can be stated that the transdermal gel according to the present invention have a liquid crystal orderliness and that this liquid crystal structure is not destroyed by the addition of hyaluronic acid.

The transdermal gel developed by us is an excellent material for the manufacturing of pharmaceutical compositions with the most versatile active agent content.

The invention relates to transdermal pharmaceutical composition consists of an estrogen and a progestin component as well as a liquid crystal gel containing Tagat TO V, propylene-glycol, isopropyl myristate and a hyaluronic acid salt or complex.

In the transdermal pharmaceutical composition according to the present invention the preferred estrogen component is estradiol, whereas the progestin component is a progestin devoid of androgenic effects (preferably gestodene, etonogestrel or levonorgestrel).

The chemical name of estradiol (also referred to as 17-β-estradiol) is 3,17β-dihydroxy-estr-1,3,5-triene.

The chemical name of gestodene is 13-ethyl-17-hydroxy-18,19-dinor-17α-pregn-4,15-diene-20-in-3-on.

The chemical name of etonogestrel (also referred to as 3-keto-dezogestrel) is 13-ethyl-17-hydroxy-11-methylene-18,19-dinor-17α-pregn-4-en-20-in-3-on.

The chemical name of levonorgestrel is 13-ethyl-17-hydroxy-18,19-dinor-17β0 -pregn-4en-20-in-3-on.

In the liquid crystal transdermal gel pharmaceutical composition according to the present invention the estrogen and progestin components are used in the following concentration ranges: estradiol: 0.001-0.7% (w/w); gestodene: 0.001-0.5% (w/w); etonogestrel: 0.001-0.7% (w/w); levonorgestrel: 0.001-0.05% (w/w).

The release of the active agent (estrogen and progestin components) from the liquid crystal transdermal gel pharmaceutical composition according to the present invention was studied by the means of a Microette Hanson vertical diffusion cell (Hanson Research Corp., USA), which on the basis of a preset protocol operated with automatic sampling.

The essence of the Hanson cell study is the following: The active agent dissolved in the gel diffuses to the membrane and partitions between the membrane and the vehicle. Crossing the membrane, the substance is subject to another partition, this time between the membrane and the acceptor phase, which is an aqueous system. The study was accomplished using a CM type, Macherey Nagel porafil membrane filter made of cellulose ether with 0.2 μm pore size and a diameter of 2.5 cm, soaked with isopropyl myristate. Thereby the membrane models better the lipophilic structure of the skin. The experiments were done with 6 parallel cells at 450 r.p.m. and at a temperature of 32° C. Sampling volume was 0.8 ml and the volume of the washing fluid was 0.5 ml. The sampling times were the following: $0.5^h$; $1^h$; $2^h$, $3^h$, $4^h$, $5^h$, $6^h$.

The steroid content of the samples collected was determined by an HPLC method. The HPLC instrument was a Hewlett-Packard 1090 model equipped with three DR5 medium pressure pumps and a HP-1090 DAD diode-array detector. The HP-Chemistation (Ver. 4.01) controlling, data acquisition and data processing application run on a DTK 081 Pentium II personal computer. The chromatographic conditions were the followings: LiChroCart 125-4, Purospher RP18e 5 μm (Merck 968264) was used as chromatographic column. The mobile phase was the mixture of acetonitrile and water in which the proportion of the acetonitrile was varied according to the following gradient program: initial: $0-30^{th}$ minute: 20-80%, $30^{th}$-$31^{st}$ minute 80-100%, $31^{st}$-$36^{th}$ minute 100%. The flow-rate, column temperature and detection wavelength were 1 ml/min, 35° C. and 205-244 nm, respectively.

For stability test of the gel according to the present invention the gel samples were kept for 2 months in a thermostat operating at 40° C. and at a relative humidity of 75%. At the end of the storage period the samples were examined in the above active agent release tests.

Some representative test results are shown below:

Gels containing different excipient compositions and 0.1% estradiol and 0.05% gestodene as active agent were tested.

The liquid crystal gels according to the present invention, which were tested had the following composition:

| | |
|---|---|
| Estradiol | 0.10% |
| Gestodene | 0.05% |
| Tagat TO V | 33.30% |
| Propylene-glycol | 16.70% |
| Isopropyl myristate | 19.00% |
| Ethanol | 5.00% |
| Benzyl alcohol | 1.00% |

-continued

| | |
|---|---|
| Hyaluronic acid salt or complex | 0.10% |
| Supplemented with purified water ad | 100.0% |

In our experiments the liquid crystal gel was produced by using three different types of hyaluronic acid salt or complex. They were: hyaluronic acid zinc complex (molecular weight: 600,000-650,000), low molecular weight (580,000-620,000) sodium-hyaluronate and high molecular weight (1,350,000-1400000) sodium-hyaluronate. The experiments allowed comparisons between the use of zinc and sodium derivative and between the application of the low and high molecular weight sodium-hyaluronate.

As a reference gel, we prepared a Carbopol-based gel with high ethanol content and the following exact composition:

| | |
|---|---|
| Estradiol | 0.10% |
| Gestodene | 0.05% |
| Carbopol | 0.20% |
| Triethanolamine | 0.30% |
| Ethanol | 40.00% |
| Supplemented with purified water ad | 100.0% |

400 milligram portion of both the freshly prepared gel samples and those stored at 40° C. for 2 months were measured into each Hanson cell, thus the estradiol and gestodene content of the samples examined was 400 μg and 200 μg, respectively. Table 1 demonstrates the area-normalized amount of estradiol diffused across the membrane by the 4$^{th}$ hour, whereas Table 2 shows the same values for gestodene. (The 4-hour sampling time was selected because it was considered unlikely that the gel would remain on the skin for longer than 4 hours.)

As it is shown by the results in Table 1 and 2 the highest active agent release for both estradiol and gestodene was obtained with the hyaluronic acid zinc complex-containing liquid crystal gel. The active agent release from the liquid crystal gel containing low molecular weight sodium-hyaluronate was not different markedly. The active agent release was lower only from the liquid crystal gel prepared with high molecular weight sodium-hyaluronate, however the difference was not significant.

TABLE 1

Estradiol release from gel formulations of various excipient composition and 0.1% estradiol and 0.05% gestodene content

| | Estradiol release during 4 hours (μg/cm$^2$) | |
|---|---|---|
| Excipient composition of the gel | Fresh gel | 2 months old gel (stored at 40° C.) |
| Liquid crystal gel according to the present invention with low molecular weight sodium-hyaluronate | 9.29 | 9.17 |
| Liquid crystal gel according to the present invention with high molecular weight sodium-hyaluronate | 7.85 | 7.88 |
| Liquid crystal gel according to the present invention containing hyaluronic acid zinc complex | 9.95 | 8.86 |
| Reference gel containing Carbopol and 40% ethanol | 5.44 | 4.16 |

The lowest active agent release was obtained with the Carbopol-containing reference gel, which could be attributed primarily to the adsorption of the active agent. In the aqueous-alcoholic Carbopol gel the majority of the active agent is present in the form of suspension. In order to be able to diffuse the active agent should first be dissolved.

As indicators of gel stability, the figures in Tables 1 and 2 demonstrate that a 2-month storage at 40° C. did not decrease the release of the active agent to any significant extent.

The results in Tables 1 and 2 also demonstrated that as vehicles, the liquid crystal gels according to the present invention either with hyaluronic acid zinc complex or sodium-hyaluronate are superior to the Carbopol-based aqueous-alcoholic gel.

TABLE 2

Gestodene release from gel formulations of various excipient composition and 0.1% estradiol and 0.05% gestodene content

| | Gestodene release during 4 hours (μg/cm$^2$) | |
|---|---|---|
| Excipient composition of the gel | Fresh gel | 2 months old gel (stored at 40° C.) |
| Liquid crystal gel according to the present invention with low molecular weight sodium-hyaluronate | 10.04 | 9.29 |
| Liquid crystal gel according to the present invention with high molecular weight sodium-hyaluronate | 6.83 | 6.83 |
| Liquid crystal gel according to the present invention containing hyaluronic acid zinc complex | 10.46 | 9.36 |
| Reference gel containing Carbopol and 40% ethanol | 2.18 | 2.33 |

The active agent release (estrogen and progestin components) from the liquid crystal transdermal gel pharmaceutical composition according to the present invention was also studied in a Hanson cell study in the presence of etonogestrel. The stability was again tested in the same study by investigating the active agent release from the gel compositions stored at 40° C. for months. In this case the liquid crystal gel had the following composition:

| | |
|---|---|
| Estradiol | 0.10% |
| Etonogestrel | 0.05% |
| Tagat TO V | 33.30% |
| Propylene-glycol | 16.70% |
| Isopropyl myristate | 19.00% |
| Ethanol | 5.00% |
| Benzyl alcohol | 1.00% |
| Hyaluronic acid zinc complex | 0.10% |
| Supplemented with purified water ad | 100.0% |

The results obtained as the function of time in the active agent release and stability tests of the above estradiol- and etonogestrel-containing combined gel composition are shown in FIG. 5 for estradiol and in FIG. 6 for etonogestrel. The x-axis indicates the time in hours, i.e. the sampling times in the Hanson cell experiments. The y-axis shows the amount of the active agent released (estradiol in FIG. 5 and etonogestrel in FIG. 6) in μg/cm$^2$ units. Both figures demonstrate the active agent release curves obtained for fresh and 2 month old gels.

As it is apparent from the results presented in FIGS. 5 and 6, in the Hanson cell model the two active agents showed an even release during the 6 hours long sampling period. Furthermore, FIGS. 5 and 6 also demonstrate that compared to the fresh gel, a 2 months long storage at 40° C. did not affect the release of the active agents from the gel.

The effect of the sodium-hyaluronate content on the release of the active agent (estrogen and progestin component) from the gel was tested in another experiment including stability testing investigated by measuring the active agent release from the same gel compositions stored at 40° C. for 2 months. The Hanson cell study was carried out with liquid crystal transdermal gel pharmaceutical compositions containing low and high molecular weight sodium-hyaluronate. The liquid crystal gels tested in this experiment were prepared with three different sodium-hyaluronate compositions: with 0.10% low molecular weight (580,000-620,000) sodium-hyaluronate, 0.10% high molecular weight (1,350,000-1,400,000) sodium-hyaluronate and with 0.05% high molecular weight (1,350,000-1,400,000) sodium-hyaluronate.

In this experiment the composition of the liquid crystal gel according to the present invention was as follows:

| | |
|---|---|
| Estradiol | 0.10% |
| Gestodene | 0.05% |
| Tagat TO V | 33.30% |
| Propylene-glycol | 16.70% |
| Isopropyl myristate | 19.00% |
| Ethanol | 5.00% |
| Benzyl alcohol | 1.00% |
| Sodium-hyaluronate (low and high molecular weight) | 0.10%, and 0.05% |
| Supplemented with purified water ad | 100.0% |

400 milligrams portions of both the freshly prepared gel samples and those stored at 40° C. for 2 months were measured into each Hanson cell, thus the estradiol and gestodene content of the samples examined was 400 µg and 200 µg, respectively. Table 3 demonstrates the area-normalized amount of estradiol diffused across the membrane by the $4^{th}$ hour, whereas Table 4 shows the same values for gestodene.

TABLE 3

Estradiol release from gel formulations with varying sodium-hyaluronate composition and 0.1% estradiol and 0.05% gestodene content

| | Estradiol release during 4 hours ($\mu g/cm^2$) | |
|---|---|---|
| Sodium-hyaluronate composition of the gel | Fresh gel | 2 months old gel (stored at 40° C.) |
| Liquid crystal gel according to the present invention with 0.10% low molecular weight sodium-hyaluronate | 9.29 | 9.17 |
| Liquid crystal gel according to the present invention with 0.10% high molecular weight sodium-hyaluronate | 7.85 | 7.88 |
| Liquid crystal gel according to the present invention with 0.05% high molecular weight sodium-hyaluronate | 10.50 | 7.98 |

As it is shown by the results in Table 3 and 4 the active agent release from the gel containing 0.10% of low molecular weight sodium-hyaluronate is about the same as that observed with the gel containing high molecular weight sodium-hyaluronate at one-half, i.e. 0.05% concentration.

Furthermore, it is also apparent from the results presented in Tables 3 and 4 that high molecular weight sodium-hyaluronate gives lower active agent release than the low molecular weight do if used at the same concentration level (0.10%). The phenomenon can possibly be explained by the adsorption of the active agent to the polymer.

In conclusion, the experimental results indicate that the active agent release from the liquid crystal transdermal gel according to the present invention is influenced by both the molecular mass and the concentration of the polymeric molecule.

TABLE 4

Gestodene release from gel formulations with varying sodium-hyaluronate composition and 0.1% estradiol and 0.05% gestodene content

| | Gestodene release during 4 hours ($\mu g/cm^2$) | |
|---|---|---|
| Sodium-hyaluronate composition of the gel | Fresh gel | 2 months old gel (stored at 40° C.) |
| Liquid crystal gel according to the present invention with 0.10% low molecular weight sodium-hyaluronate | 10.04 | 7.51 |
| Liquid crystal gel according to the present invention with 0.10% high molecular weight sodium-hyaluronate | 6.83 | 6.83 |
| Liquid crystal gel according to the present invention with 0.05% high molecular weight sodium-hyaluronate | 8.80 | 7.50 |

The invention also relates to method of treatment for transdermal hormone replacement therapy, where a pharmaceutical compositions consists of an estrogen and a progestin component as well as a liquid crystal gel containing Tagat TO V, propylene-glycol, isopropyl myristate and a hyaluronic acid salt or complex is applied onto the surface to be treated.

The transdermal application of the pharmaceutical compositions manufactured with the liquid crystal gel according to the present invention is preferably recommended in the methods of treatment listed below:

1. Treatment of the moderate to severe vasomotor symptoms, hot flush, nocturnal sweating and palpitation due to post-menopausal estrogen deficiency.
2. Treatment of the symptoms of urogenital atrophy, vaginal dryness, recurrent vaginitis, recurrent cystitis, painful intercourse and incontinence due to post-menopausal estrogen deficiency.
3. Treatment of the psychic symptoms and decreased physical performance manifesting as tiredness, anxiety, panic, irritability, lethargy, depression, mood disorders, sleep disturbances, memory problems, difficulty in mental concentration and decreased libido due to post-menopausal estrogen deficiency.
4. Treatment of estrogen deficiency due to primary ovary insufficiency or castration.
5. Treatment of dysmenorrhoea related to hormonal disorders without organic alterations and with hypoplastic endometrium.
6. Prevention of post-menopausal osteoporosis.
7. For the reduction of the size of uterine myoma and for the treatment of bleeding disorders in post-menopausal women.
8. Alleviation of the symptoms of post-menopausal estrogen deficiency in unstable hypertension.
9. Alleviation of the symptoms of post-menopausal estrogen deficiency in women with hypertriglyceridaemia
10. Alleviation of the symptoms of post-menopausal estrogen deficiency in women with a history of thromboembolism.

11. Alleviation of the symptoms of post-menopausal estrogen deficiency in women with hyperandrogenic symptoms (androgenic type alopecia, hirsutism).
12. Alleviation of the symptoms of post-menopausal estrogen deficiency in the early post-operative period of surgical menopause.
13. Alleviation of the symptoms of post-menopausal estrogen deficiency in post-menopausal women with type 2 diabetes.
14. Alleviation of the symptoms of post-menopausal estrogen deficiency in women, who cannot tolerate the side-effects of oral drug administration.
15. Alleviation of the symptoms of post-menopausal estrogen deficiency in women, who cannot tolerate the side-effects associated with transdermal patches.
16. Alleviation of the symptoms of post-menopausal estrogen deficiency in women, who cannot tolerate the side-effects associated with the use of alcohol-based transdermal gel.

In contrast to the alcohol-based aqueous gels, the estradiol- and progestin-containing liquid crystal gel developed by us contains the hormone components in solution, which increases the rate and extent of hormone absorption into the stratum corneum. A portion of estradiol gets right into the systemic circulation, whereas another portion forms a depot in stratum corneum and it is absorbed gradually into the circulation. The serum level peak associated with the oral drug administration can thus be avoided and the treatment does not result in higher than physiological hormone levels in the liver.

Compared to the alcohol-based aqueous gels, the liquid crystal gel developed by us causes less skin irritation.

The new, selective progestin hormone component of the liquid crystal gel developed by us makes progestin substitution by other routes unnecessary.

As an additional advantage, the liquid crystal gel with hormone combination can be applied on smaller surface area (150-200 cm$^2$) than that required by the alcohol-based aqueous gels (200-400 cm$^2$).

The invention also relates to transdermal pharmaceutical composition consists of one or more active agent components (among others, ondansetron, terbinafine, fluconazole, metronidazole, fentanyl, nandrolone decanoate, nestorone, norethisterone, eperisone, tolperisone, vinpocetine, ketamine, vincristine, vinblastine) and a liquid crystal gel containing Tagat TO V, propylene-glycol, isopropyl myristate as well as a hyaluronic acid salt or complex.

The chemical name of ondansetron is 1,2,3,9-tetrahydro-9-methyl-3-[(2-methyl-1H-imidazol-1-il)-methyl]-4H-karbazol-4-on.

The chemical name of terbinafine is N-(6,6-dimethyl-2-heptene-4-inyl)-N-methyl-(E)-naphtal-1-en-methan-amine.

The chemical name of fluconazole is α-(2,4-difluoro-phenyl)-α-(1H-1,2,4-triazolo-1-ilmethyl)-1H-1,2,4triazolo-1-ethanol.

The chemical name of metronidazole is 1-(2-hydroxy-1-ethyl)-2-methyl-5-nitro-imidazol.

The chemical name of fentanyl is N-[1-(phenyl-ethyl)-4-piperidyl]-propionanilide hydrochloride.

The chemical name of nandrolone decanoate is 17β-hydroxy-estr-4-ene-3-on decanoate.

The chemical name of nestorone is 16-methylene-17α-hydroxy-19-norpregn-4-ene-3.20-dion acetate.

The chemical name of norethisterone is 17-hydroxy-19-nor-17α-pregn-4-ene-20-in-3-on.

The chemical name of eperisone is 1-(4-ethyl-phenyl)-2-methyl-3-(1-piperidinyl)-1-propanon.

The chemical name of tolperisone is 1-piperidino-2-methyl-3-(p-tolyl)-3-propanon.

The chemical name of vinpocetine is (3α,16α)-eburnamenine-14-carboxylic acid ethylester.

The chemical name of ketamine is 2-(2-chloro-phenyl)-2-(methyl-amino)-cyclohexanon.

The chemical name of vincristine is 22-oxo-vincaleukoblastine.

The chemical name of vinblastine is 22-(cyclohexyl-oxy)-vincaleukoblastine.

In the transdermal pharmaceutical compositions containing ondansetron as active agent component according to the present invention the proportion of ondansetron amounts to 0.001-1.2% (w/w) of the total weight of the gel.

In the transdermal pharmaceutical compositions containing terbinafine as active agent component according to the present invention the proportion of terbinafine amounts to 0.001-2% (w/w) of the total weight of the gel.

In the transdermal pharmaceutical compositions containing fluconazole as active agent component according to the present invention the proportion of fluconazole amounts to 0.001-2.5% (w/w) of the total weight of the gel.

In the transdermal pharmaceutical compositions containing metronidazole as active agent component according to the present invention the proportion of metronidazole amounts to 0.001-0.9% (w/w) of the total weight of the gel.

In the transdermal pharmaceutical compositions containing fentanyl as active agent component according to the present invention the proportion of fentanyl amounts to 0.001-1.0% (w/w) of the total weight of the gel.

In the transdermal pharmaceutical compositions containing nandrolone decanoate as active agent component according to the present invention the proportion of nandrolone decanoate amounts to 0.001-4.5% (w/w) of the total weight of the gel.

In the transdermal pharmaceutical compositions containing nestorone as active agent component according to the present invention the proportion of nestorone amounts to 0.001-2.0% (w/w) of the total weight of the gel.

In the transdermal pharmaceutical compositions containing norethisterone as active agent component according to the present invention the proportion of norethisterone amounts to 0.001-0.5% (w/w) of the total weight of the gel.

In the transdermal pharmaceutical compositions containing eperisone as active agent component according to the present invention the proportion of eperisone amounts to 0.001-0.8% (w/w) of the total weight of the gel.

In the transdermal pharmaceutical compositions containing tolperisone as active agent component according to the present invention the proportion of tolperisone amounts to 0.001-2.0% (w/w) of the total weight of the gel.

In the transdermal pharmaceutical compositions containing vinpocetine as active agent component according to the present invention the proportion of vinpocetine amounts to 0.001-0.6% (w/w) of the total weight of the gel.

In the transdermal pharmaceutical compositions containing ketamine as active agent component according to the present invention the proportion of ketamine amounts to 0.001-1.0% (w/w) of the total weight of the gel.

In the transdermal pharmaceutical compositions containing vincristine as active agent component according to the present invention the proportion of vincristine amounts to 0.001-1.0% (w/w) of the total weight of the gel.

In the transdermal pharmaceutical compositions containing vinblastine as active agent component according to the present invention the proportion of vinblastine amounts to 0.001-0.1% (w/w) of the total weight of the gel.

We studied the release of active agents (ondansetron, terbinafine, metronidazole, eperisone, tolperisone, ketamine) in a liquid crystal transdermal gel pharmaceutical composition according to the invention and we studied the rheological and microscopic properties as well as the stability of the gel.

In addition to the 1.2% ondansetron or 2.0% terbinafine or 0.9% metronidazole or 0.8% eperisone or 1.0 and 2.0% tolperisone or 1.0% ketamine active agent content the composition of the liquid crystal gel pharmaceutical composition according to the invention used in the experiments was the following:

| | |
|---|---|
| Tagat TO V | 33.30% |
| Propylene-glycol | 16.70% |
| Isopropyl myristate | 19.00% |
| Ethanol | 0.10% |
| Benzyl alcohol | 1.00% |
| Sodium-hyaluronate (low molecular weight) | 0.10% |
| Supplemented with purified water to | 100.0% |

Preparation of the experimental gel samples was done by adding the active agent to the lipophilic basic system (Tagat TO V, propylene-glycol, isopropyl myristate, benzyl alcohol) and mixing the suspension in an ultrasonic water bath for 15 minutes. The hydrophilic phase of the system (ethanol, sodium-hyaluronate solution, water) was then added to obtain a clear, transparent, shape-preserving gel in every case. The active agents (ondansetron, terbinafine, metronidazole, eperisone, tolperisone, ketamine) used proved to be well incorporable in the gel without causing any unfavourable macroscopic change in the pleasant appearance of the transparent gel system.

Previously we studied the release of the active agents (ondansetron, terbinafine, metronidazole, eperisone, tolperisone, ketamine) by the Microette Hanson vertical diffusion cell method described in the study of steroid gel samples. The difference was that the experiments were done both with lipophilic membrane soaked with isopropyl myristate used until now and with hydrophilic membrane soaked with water. We conducted 4 parallel experiments for each active agent.

The results of the active agent release tests obtained with the above liquid crystal gels containing either ondansetron, or terbinafine, or metronidazole, or eperisone or tolperisone are presented as the function of time in FIGS. 7-14. The abscissa indicates the time in hours that corresponds the sampling times used in the Hanson cell experiments. The ordinate indicates the quantity of the released active agent in units of µg/cm² Accordingly, the active agent release for ondansetron on hydrophilic membrane is demonstrated in FIG. 7, for terbinafine on hydrophilic membrane in FIG. 8, for metronidazole on hydrophilic membrane in FIG. 9, for metronidazole on lipophilic membrane in FIG. 10, for eperisone on hydrophilic membrane in FIG. 11, for eperisone on lipophilic membrane in FIG. 12, tolperisone on hydrophilic membrane in FIG. 13, and for tolperisone on lipophilic membrane in FIG. 14.

From the results presented in FIGS. 7-14 it is apparent that in the Hanson cell model the active agents (ondansetron, terbinafine, metronidazole, eperisone, tolperisone) showed an even release during the 6-hour test period.

From the results of the active agent release experiments presented in FIGS. 7-14 it is also apparent that the compounds (for example ondansetron, terbinafine, ketamine) of hydrophilic character dissolving well or moderately in water cross the hydrophilic membrane quickly and effectively, but—obviously due to the poor partition—do not cross the membrane impregnated with lipophilic fluid. Metronidazole, eperisone, tolperisone are all able to cross both hydrophilic and lipophilic membranes but characteristically in different quantities. Significantly higher quantity of the active agent crosses the hydrophilic membrane.

From the course of the curve one may conclude that the diffusion process can be described by the following exponential function:

$$Q = Q_0 t^m \text{ where}$$

t: time,

Q: the quantity of the active agent liberated (crossed the membrane) in time t relative to unit membrane surface (1 cm²), $Q_0$: quantity of the active agent belonging to t=0 time (the value of this is theoretically 0, in the experiments however we often get a negative value that refers to a primary saturation of the membrane with the crossing active agent and that the active agent appears in the acceptor phase following complete saturation), m: rate constant of the process that is generally a number below 1.

If the value of m is approximately 0.5 the process can be linearised based on the Higuchi-like square root relationship:

$$Q = Q_0 + nt^{0.5} \text{ where}$$

n: rate constant of liberation.

We can say that in the liquid crystal transdermal gel pharmaceutical compositions prepared by us according to the invention the release kinetics of the active agents (ondansetron, terbinafine, metronidazole, eperisone, tolperisone, ketamine) generally follows the Higuchi-like relationship.

TABLE 5

Active agent release from gels of liquid crystal structure according to the invention containing different active agent

| Active agent composition of the gel | | Active agent release in 4 hours (µg/cm²) | |
|---|---|---|---|
| Name | % | Hydrophilic membrane | Lipophilic membrane |
| Ondansetron | 1.2 | 104.5 | — |
| Terbinafine | 2.0 | 2189.3 | — |
| Metronidazole | 0.9 | 390.9 | 146.50 |
| Eperisone | 0.8 | 94.8 | 15.88 |
| Tolperisone | 1.0 | 146.0 | 23.29 |
| Tolperisone | 2.0 | 247.9 | 27.07 |
| Ketamine | 1.0 | 9.73 | — |

The quantity of the active agent (ondansetron, terbinafine, metronidazole, eperisone, tolperisone, ketamine) that crossed the hydrophilic or lipophilic membrane per surface unit until the 4th hour of the experiment is demonstrated in Table 5.

From the results of the active agent release experiments presented in Table 5 it is clear that in the course of the test both terbinafine and metronidazole were released in significant quantities and crossed the hydrophilic membrane. In the case of tolperisone the concentration of the active agent in the gel does not influence the process of release because from the gel containing 1% tolperisone approximately as much is liberated from the lipophilic membrane as from the one containing 2% active agent. From the tested active agents ketamine was released from or crossed the membrane of the Hanson apparatus to the least degree.

We have done viscosity measurements of the above gel samples. The dissolved active agents do not change in an irreversible manner the Theological properties of the gel samples. The above gel samples were examined by Leica image analyzer microscopically, too, thereby we proved by an optical method the structure of the gel system according to the invention. The microscopic images proved that the samples have an optically visualisable structure and in the image the "Maltese cross" can be seen, too, as an indication of the liquid crystal character.

For the purpose of stability test we stored the liquid crystal gel samples (ondansetron, terbinafine, metronidazole, eperisone, tolperisone, ketamine) according to the invention at room temperature, at 2-5° C. and 40° C. for 2 months in well sealed glass containers then after keeping them at room temperature for 1 day macroscopic observation (visual inspection and comparison to samples stored at room temperature), rheological examination (recording of flow curves under identical circumstances as those of the measurement made after preparation) and centrifugation was done with the sample (with Janetzki K23 angle rotor centrifuge, at 3000 r.p.m. for 10 minutes.).

We can say that in the course of the 2-month storage at room temperature and at a lower temperature (2-5° C.) no change was seen in the physical properties of the liquid crystal gel according to the invention but at a higher temperature (40° C.) a small degree of softening was experienced, although no irreversible change occurred. Macroscopically (by spreading it on the skin) no change could be observed. The samples kept their good spreading properties.

Under centrifugation all samples proved to be stable, no liquid separation, no turbidity or any other macroscopic change was observed.

The invention also relates to method of treatment for transdermal therapies, where a pharmaceutical composition consists of one or more active agent components (among others, ondansetron, terbinafine, fluconazole, metronidazole, fentanyl, nandrolone decanoate, nestorone, norethisterone, eperisone, tolperisone, vinpocetine, ketamine, vincristine, vinblastine) as well as a liquid crystal gel containing Tagat TO V, propylene-glycol, isopropyl myristate and a hyaluronic acid salt or complex is applied onto the surface to be treated.

Transdermal application is a favourable route of administration for ondasetron since it offers therapeutic advantage if the active agent bypasses the gastrointestinal tract in the highly emetic chemotherapeutic treatment or surgical interventions with emetic effects (e.g. gynaecological, head and neck, gastrointestinal surgeries). Ondasetron, the selective 5-HT3-receptor antagonist, is widely used with oral or intravenous administration as an antiemetic drug during chemotherapy with strongly emetic drugs (cisplatin, carboplatin) and in the case of surgical intervention with emetic effects (related to the agents used for premedication in general anaesthesia or to the biogenic substances released during the surgical intervention). The intravenous administration is considered invasive and requires medical control. The oral administration implying drug intake with some water may in itself, through fluid intake, induce emesis in patients being treated with highly emetic chemotherapeutic agents and fluid intake is often undesirable prior to surgical interventions. Similarly to other perlingual or buccal preparations taken without water, the transdermal administration is advantageous in decreasing the risk of emesis.

When administered in transdermal drug delivery system, the antimycotic effect of terbinafine, fluconazole and metronidazole and the antibacterial effect of metronidazole against anaerobic bacteria develop locally, but in the case of a good transdermal absorption also systemically. Regarding terbinafine, its application with cream, solution and gel is widespread in the clinical practice, but only for topical treatment. Owing to their high alcohol content local side-effects are frequent with these formulations. The gel type transdermal formulation that is also suitable for forming systemic effect can advantageously be used to treat more severe skin infections. In the case of a good transdermal absorption combined local and systemic effect can be achieved with all the three active agents. Concerning fluconazole, the transdermal application provides the means to avoid drug interactions appearing due to the inhibition cytochrome P-450 enzymes by fluconazole during its first-pass metabolism. In the case of metronidazole, transdermal application may decrease the gastrointestinal side-effects (nausea, vomiting and metallic taste) associated with oral administration.

Fentanyl, the opioid analgesics, is used by systemic, intravenous and intramuscular administration but it is also applied with transdermal patches. The systemic administration is an invasive intervention and requires medical supervision. Fentanyl has but a short duration of action, therefore, it is primarily used in pre- and post-operative analgesia. The use of fentanyl patches (Durogesic TTS) offers prolonged analgesia lasting for 72 hours, however it is not suitable for the alleviation of acute pain. In contrast, the administration of fentanyl with transdermal gel provides the required analgesia both in pain syndromes and in the case of an acute pain and it makes the invasive administration unnecessary.

Androgenic, anabolic agents as well as progestin compounds (like nandrolone decanoate, nestorone and norethisterone, respectively) are often applied in small doses through transdermal patches in order to circumvent problem of poor bioavailability, i.e. the low active agent levels due to the intensive first-pass metabolism. Owing to their adhesive components, patch type transdermal compositions, however, often cause local skin irritation, whereby the site of application should be changed frequently. Using the transdermal pharmaceutical compositions designed for hormone replacement therapy and anabolic treatment according to the present invention the local irritation can be avoided.

The use of the gel-based transdermal drug delivery system is advantageous also in the case of centrally acting, local anaesthetic type, sodium-channel blocker muscle relaxants (eperisone, tolperisone), since lower first-pass metabolism, thus improved bioavailability can be achieved this way. Both active agents have a very low bioavailability and both are subject to an intensive metabolism after oral administration. A transdermal patch formulation has already been developed for eperisone.

Transdermal drug administration can favourably increase the very low (6-8%) bioavailability of vinpocetine, the active agent, which improves cerebral metabolism and microcirculation. Compared to the oral administration, transdermal application ensures that more active agent reaches the systemic circulation, since its metabolism decreases though bypassing the gastrointestinal tract and the liver.

In contrast to the current practice of intravenous administration that requires medical control and also hospitalisation in a number of cases, the analgesic effect of the NMDA antagonist, ketamine, can be achieved in out-patient settings. Here again, transdermal application can circumvent the poor oral bioavailability of the drug.

There are publications demonstrating that via iontophoretic topical administration vincristine and vinblastine— the chemotherapeutic agents applicable by systemic administration—can be used as effective analgesics in various pain syndromes since they can destroy nerve endings (Csillik, B. et al.: Neurosci. Letters, Vol. 31. p. 87-90. 1982 and Knyihar-Csillik, E. et al.: Acta Neurol. Scandinav.; Vol. 66. p. 401-412. 1982). These active agents can effectively treat pain syndromes also when administered in a transdermal drug delivery system, which makes the use of iontophoresis unnecessary and helps avoiding the side-effects associated with systemic administration.

The transdermal application of the liquid crystal gel pharmaceutical compositions according to the present invention is especially recommended in the methods of treatment listed below:

Method of treatment for transdermal antiemetic therapy during strongly emetic chemotherapy and surgical interventions, in which a pharmaceutical composition consists of ondansetron as well as a liquid crystal gel containing Tagat TO V, propylene-glycol, isopropyl myristate and a hyaluronic acid salt or complex is applied onto the surface to be treated.

Method of treatment for transdermal antimycotic therapy, in which a pharmaceutical composition consists of terbinafine as well as a liquid crystal gel containing Tagat TO V, propylene-glycol, isopropyl myristate and a hyaluronic acid salt or complex is applied onto the surface to be treated.

Method of treatment for transdermal antimycotic therapy, in which a pharmaceutical composition consists of fluconazole as well as a liquid crystal gel containing Tagat TO V, propylene-glycol, isopropyl myristate and a hyaluronic acid salt or complex is applied onto the surface to be treated.

Method of treatment for transdermal antimycotic therapy and antibacterial therapy against anaerobic pathogens and trichomonas, in which a pharmaceutical composition consists of metronidazole as well as a liquid crystal gel containing Tagat TO V, propylene-glycol, isopropyl myristate and a hyaluronic acid salt or complex is applied onto the surface to be treated.

Method of treatment for transdermal analgesic therapy in pain syndromes and in other acute pain, in which a pharmaceutical composition consists of fentanyl as well as a liquid crystal gel containing Tagat TO V, propylene-glycol, isopropyl myristate and a hyaluronic acid salt or complex is applied onto the surface to be treated.

Method of treatment for transdermal hormone replacement and anabolic therapy, in which a pharmaceutical composition consists of nandrolone decanoate as well as a liquid crystal gel containing Tagat TO V, propylene-glycol, isopropyl myristate and a hyaluronic acid salt or complex is applied onto the surface to be treated.

Method of treatment for transdermal hormone replacement and anabolic therapy, in which a pharmaceutical composition consists of nestorone as well as a liquid crystal gel containing Tagat TO V, propylene-glycol, isopropyl myristate and a hyaluronic acid salt or complex is applied onto the surface to be treated.

Method of treatment for transdermal hormone replacement and anabolic therapy, in which a pharmaceutical composition consists of norethisterone as well as a liquid crystal gel containing Tagat TO V, propylene-glycol, isopropyl myristate and a hyaluronic acid salt or complex is applied onto the surface to be treated.

Method of treatment for transdermal muscle relaxant therapy, in which a pharmaceutical composition consists of eperisone as well as a liquid crystal gel containing Tagat TO V, propylene-glycol, isopropyl myristate and a hyaluronic acid salt or complex is applied onto the surface to be treated.

Method of treatment for transdermal muscle relaxant therapy, in which a pharmaceutical composition consists of tolperisone as well as a liquid crystal gel containing Tagat TO V, propylene-glycol, isopropyl myristate and a hyaluronic acid salt or complex is applied onto the surface to be treated.

Method of treatment for transdermal therapy to improve cerebral metabolism and microcirculation, in which a pharmaceutical composition consists of vinpocetine as well as a liquid crystal gel containing Tagat TO V, propylene-glycol, isopropyl myristate and a hyaluronic acid salt or complex is applied onto the surface to be treated.

Method of treatment for transdermal analgesic therapy, in which a pharmaceutical composition consists of ketamine as well as a liquid crystal gel containing Tagat TO V, propylene-glycol, isopropyl myristate and a hyaluronic acid salt or complex is applied onto the surface to be treated.

Method of treatment for transdermal analgesic therapy by nerve ending destruction in various pain syndromes, in which a pharmaceutical composition consists of vincristine as well as a liquid crystal gel containing Tagat TO V, propylene-glycol, isopropyl myristate and a hyaluronic acid salt or complex is applied onto the surface to be treated.

Method of treatment for transdermal analgesic therapy by nerve ending destruction in various pain syndromes, in which a pharmaceutical composition consists of vinblastine as well as a liquid crystal gel containing Tagat TO V, propylene-glycol, isopropyl myristate and a hyaluronic acid salt or complex is applied onto the surface to be treated.

In conclusion, the pharmaceutical composition developed by us is a transdermal gel that compared to those in current art offers the following advantages:

- it is suitable for the transdermal delivery of active agents with no or poor aqueous solubility,
- it contains less alcohol and thus it does not cause skin irritation;
- through the formation of a molecular dispersion system (true solution) the active agent can homogenously distributed in the gel;
- it is easy to dose;
- it is a thermodynamically stable gel;
- it is transparent, aesthetic and has an attractive appearance. In addition to the aesthetic aspect, transparency offers the advantage of the easy macroscopic recognition of any alteration (e.g. decomposition);
- the gel has liquid crystal structure,
- it is shape-preserving;
- easier and more accurate dispersion over skin of specific area;
- rapid and ready absorption into the skin;
- rapid drug release.

Further details of the present invention are shown in the following examples. These examples are not intended to limit the invention in any manner.

Examples 1-6 demonstrates the manufacturing process of the liquid crystal transdermal gel pharmaceutical composition developed by us for hormone replacement therapy.

Examples 7-32 gives several representative examples concerning the composition of the liquid crystal transdermal gel pharmaceutical composition according to the present invention for hormone replacement therapy.

Examples 33-60 demonstrates the manufacturing process of the liquid crystal transdermal gel pharmaceutical compositions developed by us to contain other active agents.

Examples 61-88 gives several representative examples concerning the composition of the liquid crystal transdermal gel pharmaceutical composition according to the present invention with various active agent content.

EXAMPLE 1

Process for the Manufacturing of Estradiol- and Gestodene-containing Liquid Crystal Transdermal Gel Pharmaceutical Composition for Hormone Replacement Therapy Into a chemically and microbiologically clean pot suitable for pharmaceutical manufacture 33.3 g Tagat TO V, 16.7 g propylene-glycol and 1.0 g benzyl alcohol are weighed at room temperature and the mixture is homogenized preferably with a mixer operating at less than 1500 r.p.m. for 5 minutes in a way that ensures the system remains free of air as far as possible. Non-aerated conditions can be ensured both by low stirring speed and preferably by the application of vacuum. The order the components are mixed can be changed.

The required amount of the active agents adjusted to 100% air-dry active agent content and corresponding to 0.10 g estradiol and 0.05 g gestodene are weighed and dissolved in 5.0 g of ethanol under continuous mixing at a speed of lower than 1500 r.p.m. Dissolution takes about 30 minutes.

The active agent solution is added to the mixture of Tagat TO V, propylene-glycol and benzyl alcohol and the mixture is homogenized by stirring at less than 1500 r.p.m. for at least 30 minutes.

To the mixture containing the active agent solution as well as the mixture of Tagat TO V, propylene-glycol and benzyl alcohol, 19.0 g of isopropyl myristate is added and the mixture is homogenized by stirring at less than 1500 r.p.m. for at least 30 minutes.

Parallel to the above process, a 1% aqueous solution is made of sodium-hyaluronate using a mixer working preferably at less than 1500 r.p.m. The solution obtained this way is a highly viscous, thick fluid. After complete swelling is attained—which takes a minimum of 1 hour, but may take as much as four hours depending on the performance of the mixer—10.0 g of the 1% aqueous solution of sodium-hyaluronate is admixed to the above mixture and the mixture obtained is made up to 100 g with purified water. The system composed this way is homogenized with a stirrer working preferably at less than 1500 r.p.m. to allow the formation of the gel structure. The duration of homogenization is at least 30 minutes. The transparent gel obtained this way is filled into appropriate containers to make it applicable.

The viscosity of the gel system produced this way is monitored using a rotation viscosimeter, while liquid crystals are identified by polarization light microscopy.

EXAMPLE 2

Process for the Manufacturing of Estradiol- and Gestodene-containing Liquid Crystal Transdermal Gel Pharmaceutical Composition for Hormone Replacement Therapy The process described in Example 1 is followed with the exception that sodium-hyaluronate is replaced by 10.0 g of a 1% aqueous solution of hyaluronic acid zinc complex.

EXAMPLE 3

Process for the Manufacturing of Estradiol- and Etonogestrel-containing Liquid Crystal Transdermal Gel Pharmaceutical Composition for Hormone Replacement Therapy The process described in Example 1 is followed with the exception that gestodene is replaced by 0.05 g of etonogestrel.

EXAMPLE 4

Process for the Manufacturing of Estradiol- and Etonogestrel-containing Liquid Crystal Transdermal Gel Pharmaceutical Composition for Hormone Replacement Therapy The process described in Example 3 is followed with the exception that sodium-hyaluronate is replaced by 10.0 g of a 1% aqueous solution of hyaluronic acid zinc complex.

EXAMPLE 5

Process for the Manufacturing of Estradiol- and Levonorgestrel-containing Liquid Crystal Transdermal Gel Pharmaceutical Composition for Hormone Replacement Therapy The process described in Example 1 is followed with the exception that gestodene is replaced by 0.05 g of levonorgestrel.

EXAMPLE 6

Process for the Manufacturing of Estradiol- and Levonorgestrel-containing Liquid Crystal Transdermal Gel Pharmaceutical Composition for Hormone Replacement Therapy The process described in Example 5 is followed with the exception that sodium-hyaluronate is replaced by 10.0 g of a 1% aqueous solution of hyaluronic acid zinc complex.

EXAMPLE 7

| | |
|---|---|
| Estradiol | 0.10 g |
| Gestodene | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 8

| | |
|---|---|
| Estradiol | 0.70 g |
| Gestodene | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 9

| | |
|---|---|
| Estradiol | 0.10 g |
| Gestodene | 0.50 g |

-continued

| | |
|---|---|
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 |

EXAMPLE 10

| | |
|---|---|
| Estradiol | 0.70 g |
| Gestodene | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 11

| | |
|---|---|
| Estradiol | 0.01 g |
| Gestodene | 0.01 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 12

| | |
|---|---|
| Estradiol | 0.10 g |
| Gestodene | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 13

| | |
|---|---|
| Estradiol | 0.70 g |
| Gestodene | 0.05 g |
| Tagat TO V | 33.30 g |
| Propylene-glycol | 16.70 g |
| Isopropyl myristate | 19.00 g |
| Ethanol | 5.00 g |

-continued

| | |
|---|---|
| Benzyl alcohol | 1.00 g |
| Hyaluronic acid zinc complex | 0.10 g |
| Supplemented with purified water ad | 100.0 g |

EXAMPLE 14

| | |
|---|---|
| Estradiol | 0.10 g |
| Gestodene | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 15

| | |
|---|---|
| Estradiol | 0.70 g |
| Gestodene | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 16

| | |
|---|---|
| Estradiol | 0.01 g |
| Gestodene | 0.01 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 17

| | |
|---|---|
| Estradiol | 0.10 g |
| Etonogestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 18

| | |
|---|---|
| Estradiol | 0.70 g |
| Etonogestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 19

| | |
|---|---|
| Estradiol | 0.10 g |
| Etonogestrel | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 20

| | |
|---|---|
| Estradiol | 0.70 g |
| Etonogestrel | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 21

| | |
|---|---|
| Estradiol | 0.01 g |
| Etonogestrel | 0.01 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 22

| | |
|---|---|
| Estradiol | 0.10 g |
| Etonogestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 23

| | |
|---|---|
| Estradiol | 0.70 g |
| Etonogestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 24

| | |
|---|---|
| Estradiol | 0.10 g |
| Etonogestrel | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 25

| | |
|---|---|
| Estradiol | 0.70 g |
| Etonogestrel | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 26

| | |
|---|---|
| Estradiol | 0.01 g |
| Etonogestrel | 0.01 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 27

| | |
|---|---|
| Estradiol | 0.10 g |
| Levonorgestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 28

| | |
|---|---|
| Estradiol | 0.70 g |
| Levonorgestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 29

| | |
|---|---|
| Estradiol | 0.01 g |
| Levonorgestrel | 0.01 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 30

| | |
|---|---|
| Estradiol | 0.10 g |
| Levonorgestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 31

| | |
|---|---|
| Estradiol | 0.70 g |
| Levonorgestrel | 0.05 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 32

| | |
|---|---|
| Estradiol | 0.01 g |
| Levonorgestrel | 0.01 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 33

Process for the Manufacturing the Ondansetron-containing Liquid Crystal Transdermal Gel Pharmaceutical Composition Into a chemically and microbiologically clean pot suitable for pharmaceutical manufacture 33.3 g Tagat TO V, 16.7 g propylene-glycol and 1.0 g benzyl alcohol are weighed at room temperature and the mixture is homogenized preferably with a mixer operating at less than 1500 r.p.m. for 5 minutes in a way that ensures the system remains free of air as far as possible. Non-aerated conditions can be ensured both by low stirring speed and preferably by the application of vacuum. The order the components are mixed can be changed.

The required amount of the active agent adjusted to 100% air-dry active agent content and corresponding to 1.2 g of ondansetron is weighed and dissolved in 25.0 g of a water:ethanol 4:1 mixture under continuous mixing at speed of lower than 1500 r.p.m. Dissolution takes about 30 minutes.

The active agent solution is added to the mixture of Tagat TO V, propylene-glycol and benzyl alcohol and the mixture is homogenized by stirring at less than 1500 r.p.m. for at least 30 minutes.

To the mixture containing the active agent solution as well as the mixture of Tagat TO V, propylene-glycol and benzyl alcohol, 19.0 g of isopropyl myristate is added at room temperature and the mixture is homogenized by stirring at less than 1500 r.p.m. for at least 30 minutes.

Parallel to the above process, a 1% aqueous solution is made of sodium-hyaluronate using a mixer working preferably at less than 1500 r.p.m. The solution obtained this way is a highly viscous, thick fluid. After complete swelling is attained—which takes a minimum of 1 hour, but may take as much as 4 hours depending on the performance of the mixer—10.0 g of the 1% aqueous solution of sodium-hyaluronate is admixed to the above mixture and the mixture obtained is made up to 100 g with purified water. The system composed this way is homogenized with a stirrer working preferably at less than 1500 r.p.m. to allow the formation of the gel structure. The duration of homogenization is at least 30 minutes. The transparent gel obtained this way is filled into appropriate containers to make it applicable.

The viscosity of the gel system produced this way is monitored using a rotation viscosimeter, while liquid crystals are identified by polarization light microscopy.

EXAMPLE 34

Process for the Manufacturing the Ondansetron-containing Liquid Crystal Transdermal Gel Pharmaceutical Composition The process described in Example 33 is followed with the exception that sodium-hyaluronate is replaced by 10.0 g of a 1% aqueous solution of hyaluronic acid zinc complex.

EXAMPLE 35

Process for the Manufacturing the Terbinafine-containing Liquid Crystal Transdermal Gel Pharmaceutical Composition The process described in Example 33 is followed with the exception that ondansetron is replaced by 2.0 g of terbinafine.

EXAMPLE 36

Process for the Manufacturing the Terbinafine-containing Liquid Crystal Transdermal Gel Pharmaceutical Composition The process described in Example 35 is followed with the exception that sodium-hyaluronate is replaced by 10.0 g of a 1% aqueous solution of hyaluronic acid zinc complex.

EXAMPLE 37

Process for the Manufacturing the Fluconazole-containing Liquid Crystal Transdermal Gel Pharmaceutical Composition The process described in Example 33 is followed with the exception that ondansetron is replaced by 2.5 g of fluconazole.

EXAMPLE 38

Process for the Manufacturing the Fluconazole-containing Liquid Crystal Transdermal Gel Pharmaceutical Composition The process described in Example 37 is followed with the exception that sodium-hyaluronate is replaced by 10.0 g of a 1% aqueous solution of hyaluronic acid zinc complex.

EXAMPLE 39

Process for the Manufacturing the Metronidazole-containing Liquid Crystal Transdermal Gel Pharmaceutical Composition The process described in Example 33 is followed with the exception that ondansetron is replaced by 0.9 g of metronidazole.

EXAMPLE 40

Process for the Manufacturing the Metronidazole-containing Liquid Crystal Transdermal Gel Pharmaceutical Composition The process described in Example 39 is followed with the exception that sodium-hyaluronate is replaced by 10.0 g of a 1% aqueous solution of hyaluronic acid zinc complex.

EXAMPLE 41

Process for the Manufacturing the Fentanyl-containing Liquid Crystal Transdermal Gel Pharmaceutical Composition The process described in Example 33 is followed with the exception that ondansetron is replaced by 1.0 g of fentanyl.

EXAMPLE 42

Process for the Manufacturing the Fentanyl-containing Liquid Crystal Transdermal Gel Pharmaceutical Composition The process described in Example 41 is followed with the exception that sodium-hyaluronate is replaced by 10.0 g of a 1% aqueous solution of hyaluronic acid zinc complex.

EXAMPLE 43

Process for the Manufacturing the Nandrolone Decanoate-containing Liquid Crystal Gel Transdermal Pharmaceutical Composition The process described in Example 33 is followed with the exception that ondansetron is replaced by 4.5 g of nandrolone decanoate.

EXAMPLE 44

Process for the Manufacturing the Nandrolone Decanoate-containing Liquid Crystal Transdermal Gel Pharmaceutical Composition The process described in Example 43 is followed with the exception that sodium-hyaluronate is replaced by 10.0 g of a 1% aqueous solution of hyaluronic acid zinc complex.

EXAMPLE 45

Process for the Manufacturing the Nestorone-containing Liquid Crystal Transdermal Gel Pharmaceutical Composition The process described in Example 33 is followed with the exception that ondansetron is replaced by 2.0 g of nestorone.

EXAMPLE 46

Process for the Manufacturing the Nestorone-containing Liquid Crystal Transdermal Gel Pharmaceutical Composition The process described in Example 45 is followed with the exception that sodium-hyaluronate is replaced by 10.0 g of a 1% aqueous solution of hyaluronic acid zinc complex.

EXAMPLE 47

Process for the Manufacturing the Norethisterone-containing Liquid Crystal Transdermal Gel Pharmaceutical Composition The process described in Example 33 is followed with the exception that ondansetron is replaced by 0.5 g of norethisterone.

EXAMPLE 48

Process for the Manufacturing the Norethisterone-containing Liquid Crystal Transdermal Gel Pharmaceutical Composition The process described in Example 47 is followed with the exception that sodium-hyaluronate is replaced by 10.0 g of a 1% aqueous solution of hyaluronic acid zinc complex.

EXAMPLE 49

Process for the Manufacturing the Eperisone-containing Liquid Crystal Transdermal Gel Pharmaceutical Composition The process described in Example 33 is followed with the exception that ondansetron is replaced by 0.8 g of eperisone.

EXAMPLE 50

Process for the Manufacturing the Eperisone-containing Liquid Crystal Transdermal Gel Pharmaceutical Composition The process described in Example 49 is followed with the exception that sodium-hyaluronate is replaced by 10.0 g of a 1% aqueous solution of hyaluronic acid zinc complex.

EXAMPLE 51

Process for the Manufacturing the Tolperisone-containing Liquid Crystal Transdermal Gel Pharmaceutical Composition The process described in Example 33 is followed with the exception that ondansetron is replaced by 2.0 g of tolperisone.

EXAMPLE 52

Process for the Manufacturing the Tolperisone-containing Liquid Crystal Transdermal Gel Pharmaceutical Composition The process described in Example 51 is followed with the exception that sodium-hyaluronate is replaced by 10.0 g of a 1% aqueous solution of hyaluronic acid zinc complex.

EXAMPLE 53

Process for the Manufacturing the Vinpocetine-containing Liquid Crystal Transdermal Gel Pharmaceutical Composition The process described in Example 33 is followed with the exception that ondansetron is replaced by 0.6 g of vinpocetine.

EXAMPLE 54

Process for the Manufacturing the Vinpocetine-containing Liquid Crystal Transdermal Gel Pharmaceutical Composition The process described in Example 53 is followed with the exception that sodium-hyaluronate is replaced by 10.0 g of a 1% aqueous solution of hyaluronic acid zinc complex.

EXAMPLE 55

Process for the Manufacturing the Ketamine-containing Liquid Crystal Transdermal Gel Pharmaceutical Composition The process described in Example 33 is followed with the exception that ondansetron is replaced by 1.0 g of ketamine.

EXAMPLE 56

Process for the Manufacturing the Ketamine-containing Liquid Crystal Transdermal Gel Pharmaceutical Composition The process described in Example 55 is followed with the exception that sodium-hyaluronate is replaced by 10.0 g of a 1% aqueous solution of hyaluronic acid zinc complex.

EXAMPLE 57

Process for the Manufacturing the Vincristine-containing Liquid Crystal Transdermal Gel Pharmaceutical Composition The process described in Example 33 is followed with the exception that ondansetron is replaced by 1.0 g of vincristine.

EXAMPLE 58

Process for the Manufacturing the Vincristine-containing Liquid Crystal Transdermal Gel Pharmaceutical Composition The process described in Example 57 is followed with the exception that sodium-hyaluronate is replaced by 10.0 g of a 1% aqueous solution of hyaluronic acid zinc complex.

EXAMPLE 59

Process for the Manufacturing the Vinblastine-containing Liquid Crystal Transdermal Gel Pharmaceutical Composition The process described in Example 33 is followed with the exception that ondansetron is replaced by 0.1 g of vinblastine.

EXAMPLE 60

Process for the Manufacturing the Vinblastine-containing Liquid Crystal Transdermal Gel Pharmaceutical Composition The process described in Example 59 is followed with the exception that sodium-hyaluronate is replaced by 10.0 g of a 1% aqueous solution of hyaluronic acid zinc complex.

EXAMPLE 61

| | |
|---|---|
| Ondansetron | 1.20 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 62

| | |
|---|---|
| Ondansetron | 1.20 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 63

| | |
|---|---|
| Terbinafine | 2.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 64

| | |
|---|---|
| Terbinafine | 2.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 65

| | |
|---|---|
| Fluconazole | 2.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 66

| | |
|---|---|
| Fluconazole | 2.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 67

| | |
|---|---|
| Metronidazole | 0.90 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 68

| | |
|---|---|
| Metronidazole | 0.90 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 69

| | |
|---|---|
| Fentanyl | 1.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 70

| | |
|---|---|
| Fentanyl | 1.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 71

| | |
|---|---|
| Nandrolone decanoate | 4.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 72

| | |
|---|---|
| Nandrolone decanoate | 4.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 73

| | |
|---|---|
| Nestorone | 2.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 74.

| | |
|---|---|
| Nestorone | 2.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 75

| | |
|---|---|
| Norethisterone | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 76

| | |
|---|---|
| Norethisterone | 0.50 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 77

| | |
|---|---|
| Eperisone | 0.80 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 78

| | |
|---|---|
| Eperisone | 0.80 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 79

| | |
|---|---|
| Tolperisone | 2.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 80

| | |
|---|---|
| Tolperisone | 2.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 81

| | |
|---|---|
| Vinpocetine | 0.60 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 82

| | |
|---|---|
| Vinpocetine | 0.60 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 83

| | |
|---|---|
| Ketamine | 1.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 84

| | |
|---|---|
| Ketamine | 1.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 85

| | |
|---|---|
| Vincristine | 1.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 86

| | |
|---|---|
| Vincristine | 1.00 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

EXAMPLE 87

| | |
|---|---|
| Vinblastine | 0.10 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Sodium-hyaluronate | 0.10 g |
| Supplemented with purified water ad | 100.0 g |

EXAMPLE 88

| | |
|---|---|
| Vinblastine | 0.10 g |
| Tagat TO V | 33.30 g |
| Propylene-glycol | 16.70 g |
| Isopropyl myristate | 19.00 g |
| Ethanol | 5.00 g |
| Benzyl alcohol | 1.00 g |
| Hyaluronic acid zinc complex | 0.10 g |
| Supplemented with purified water ad | 100.0 g |

What we claim is:

1. A liquid crystal gel for use in the manufacture of transdermal pharmaceutical compositions and healing cosmetics, which comprises:

| | |
|---|---|
| Polyoxyethylene-glyceryl-trioleate | 26.7-40.0%, |
| Propylene-glycol | 13.3-20.0%, |
| Isopropyl myristate | 5.0-35.0%, |
| Ethanol | 0.01-10.0% |
| Benzyl alcohol | 0.5-1.5%, |
| a hyaluronic acid salt or complex | 0.01-2.00%, and |
| Purified water | 12.5 to 26.5%. |

2. The liquid crystal gel defined in claim 1 wherein the hyaluronic acid salt or complex is sodium hyaluronate.

3. The liquid crystal gel defined in claim 1 wherein the hyaluronic acid salt or complex is zinc hyaluronic acid complex.

4. The liquid crystal gel defined in claim 1 wherein the ratio of polyoxyethylene-glyceryl-trioleate and propylene-glycol is 2:1.

5. The liquid crystal gel defined in claim 1 which comprises:

| | |
|---|---|
| Polyoxyethylene-glyceryl-trioleate | 30.0-35.0%, |
| Propylene-glycol | 15.0-18.0%, |
| Isopropyl myristate | 17.0-20.0%, |
| Ethanol | 4.0-6.0% |
| Benzyl alcohol | 0.7-1.3%, |
| a hyaluronic acid salt or complex | 0.05-0.15%, and |
| Purified water | 20.0 to 25.0%. |

6. The liquid crystal gel defined in claim 5 wherein the hyaluronic acid salt or complex is sodium hyaluronate having a mean molecular weight from 580,000 to 620,000 or from 1,350,000 to 1,400,000.

7. The liquid crystal gel defined in claim 5 wherein the hyaluronic acid salt or complex is zinc hyaluronic acid complex having a mean molecular weight from 600,000 to 650,000.

8. The liquid crystal gel defined in claim 6 which comprises:

| | |
|---|---|
| Polyoxyethylene-glyceryl-trioleate | 33.3%, |
| Propylene-glycol | 16.7%, |
| Isopropyl myristate | 19.0%, |
| Ethanol | 5.0% |
| Benzyl alcohol | 1.0%, |
| Sodium hyaluronate | 0.1%, and |
| Supplemented with purified water ad | 100%. |

9. The liquid crystal gel defined in claim 7 which comprises:

| | |
|---|---|
| Polyoxyethylene-glyceryl-trioleate | 33.3%, |
| Propylene-glycol | 16.7%, |
| Isopropyl myristate | 19.0%, |
| Ethanol | 5.0% |
| Benzyl alcohol | 1.0%, |
| Zinc hyaluronic acid complex | 0.1%, and |
| Supplemented with purified water ad | 100%. |

10. A transdermal pharmaceutical composition as a liquid crystal gel, which consists essentially of:
    (a) an estrogen component; and
    (b) a progestin component, as therapeutically effective ingredients wherein said estrogen component and said progestin component are included in a therapeutically effective amount sufficient for hormone replacement therapy; and
    (c) a liquid crystal gel which contains the therapeutically active ingredients, said liquid crystal gel consisting essentially of:

| | |
|---|---|
| Polyoxyethylene-glyceryl-trioleate | 26.7-40.0%, |
| Propylene-glycol | 13.3-20.0%, |
| Isopropyl myristate | 5.0-35.0%, |
| Ethanol | 0.01-10.0% |
| Benzyl alcohol | 0.5-1.5%, |
| a hyaluronic acid salt or complex | 0.01-2.00%, and |
| Purified water | 12.5 to 26.5%. |

11. The transdermal pharmaceutical composition as a liquid crystal gel defined in claim 10 wherein the estrogen component is estradiol.

12. The transdermal pharmaceutical composition as a liquid crystal gel defined in claim 10 wherein the progestin compound is gestodene.

13. The transdermal pharmaceutical composition as a liquid crystal gel defined in claim 10 wherein the progestin compound is etonogestrel.

14. The transdermal pharmaceutical composition as a liquid crystal gel defined in claim 10 wherein the progestin compound is levonorgestrel.

15. A method of treating a patient for moderate to severe vasomotor symptoms, as well as hot flashes, nocturnal sweating, and palpitation due to post-menopausal estrogen deficiency, which comprises the step of transdermally administering to the skin of the patient, a therapeutically effective amount of the transdermal pharmaceutical composition defined in claim 10.

16. A transdermal pharmaceutical composition as a liquid crystal gel, which consists essentially of:
    (a) at least one therapeutically active ingredient and
    (b) a liquid crystal gel which contains the at least one therapeutically active ingredient, said liquid crystal gel consisting essentially of:

| | |
|---|---|
| Polyoxyethylene-glyceryl-trioleate | 26.7-40.0%, |
| Propylene-glycol | 13.3-20.0%, |
| Isopropyl myristate | 5.0-35.0%, |
| Ethanol | 0.01-10.0% |
| Benzyl alcohol | 0.5-1.5%, |
| a hyaluronic acid salt or complex | 0.01-2.00%, and |
| Purified water | 12.5 to 26.5%. |

17. The transdermal pharmaceutical composition as a liquid crystal gel defined in claim 16 wherein the therapeutically active ingredient is ondansetron.

18. The transdermal pharmaceutical composition as a liquid crystal gel defined in claim 16 wherein the therapeutically active ingredient is terbinafine.

19. The transdermal pharmaceutical composition as a liquid crystal gel defined in claim 16 wherein the therapeutically active ingredient is fluconazole.

20. The transdermal pharmaceutical composition as a liquid crystal gel defined in claim 16 wherein the therapeutically active ingredient is metronidazole.

21. The transdermal pharmaceutical composition as a liquid crystal gel defined in claim 16 wherein the therapeutically active ingredient is fentanyl.

22. The transdermal pharmaceutical composition as a liquid crystal gel defined in claim 16 wherein the therapeutically active ingredient is nandrolone decanoate.

23. The transdermal pharmaceutical composition as a liquid crystal gel defined in claim 16 wherein the therapeutically active ingredient is nestorone.

24. The transdermal pharmaceutical composition as a liquid crystal gel defined in claim 16 wherein the therapeutically active ingredient is norethisterone.

25. The transdermal pharmaceutical composition as a liquid crystal gel defined in claim 16 wherein the therapeutically active ingredient is eperisone.

26. The transdermal pharmaceutical composition as a liquid crystal gel defined in claim 16 wherein the therapeutically active ingredient is tolperisone.

27. The transdermal pharmaceutical composition as a liquid crystal gel defined in claim 16 wherein the therapeutically active ingredient is vinpocetine.

28. The transdermal pharmaceutical composition as a liquid crystal gel defined in claim 16 wherein the therapeutically active ingredient is ketamine.

29. The transdermal pharmaceutical composition as a liquid crystal gel defined in claim 16 wherein the therapeutically active ingredient is vincristine.

30. The transdermal pharmaceutical composition as a liquid crystal gel defined in claim 16 wherein the therapeutically active ingredient is vinblastine.

* * * * *